(12) United States Patent
Zhao et al.

(10) Patent No.: US 11,571,673 B2
(45) Date of Patent: Feb. 7, 2023

(54) FLUID DISTRIBUTOR, REACTION DEVICE AND APPLICATION THEREOF

(71) Applicants: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

(72) Inventors: Le Zhao, Shanghai (CN); Lianghua Wu, Shanghai (CN)

(73) Assignees: China Petroleum & Chemical Corporation, Beijing (CN); Shanghai Research Institute of Petrochemical Technology SINOPEC, Shanghai (CN)

( * ) Notice: Subject to any disclaimer, the term of this patent is extended or adjusted under 35 U.S.C. 154(b) by 352 days.

(21) Appl. No.: 16/763,917

(22) PCT Filed: Nov. 9, 2018

(86) PCT No.: PCT/CN2018/114771
§ 371 (c)(1),
(2) Date: May 13, 2020

(87) PCT Pub. No.: WO2019/096065
PCT Pub. Date: May 23, 2019

(65) Prior Publication Data
US 2020/0368707 A1 Nov. 26, 2020

(30) Foreign Application Priority Data
Nov. 14, 2017 (CN) .......................... 201711128526.8

(51) Int. Cl.
*B01J 8/44* (2006.01)
*B01J 8/18* (2006.01)
*C07C 253/26* (2006.01)

(52) U.S. Cl.
CPC ............... *B01J 8/44* (2013.01); *B01J 8/1827* (2013.01); *C07C 253/26* (2013.01)

(58) Field of Classification Search
CPC ............ B01J 8/44; B01J 8/1827; B01J 4/004; B01J 4/001; B01J 4/00; B01J 8/24; C07C 253/26; C07C 255/08
(Continued)

(56) References Cited

U.S. PATENT DOCUMENTS 3,704,690 A    12/1972   Mevenkamp
4,875,996 A    10/1989   Hsieh et al.
(Continued)

FOREIGN PATENT DOCUMENTS

CN          1089596 A      7/1994
CN     202387443 U      8/2012
(Continued)

OTHER PUBLICATIONS

Maiti, R.N. et al.; Gas-Liquid Distributors for Trickle-Bed Reactors: A Review; Industrial & Engineering Chemistry Research; 2007, 46, 19, 6164-6182, Aug. 22, 2007.

*Primary Examiner* — Huy Tram Nguyen
(74) *Attorney, Agent, or Firm* — Novick, Kim & Lee, PLLC; Allen Xue

(57) ABSTRACT

A fluid distributor includes one or more fluid transport main pipe. The fluid transport main pipe is configured to assume a closed shape when its centerlines and/or centerline extensions are joined end-to-end. Each of the fluid transport main pipe has at least one fluid inlet and is connected with a plurality of fluid transport branch pipes. Each of the fluid transport branch pipes has a plurality of open pores disposed along the length of the fluid transport branch pipe and a connection portion. The connection portion is configured to connect the fluid transport branch pipe to the housing after (Continued)

Figure 1:
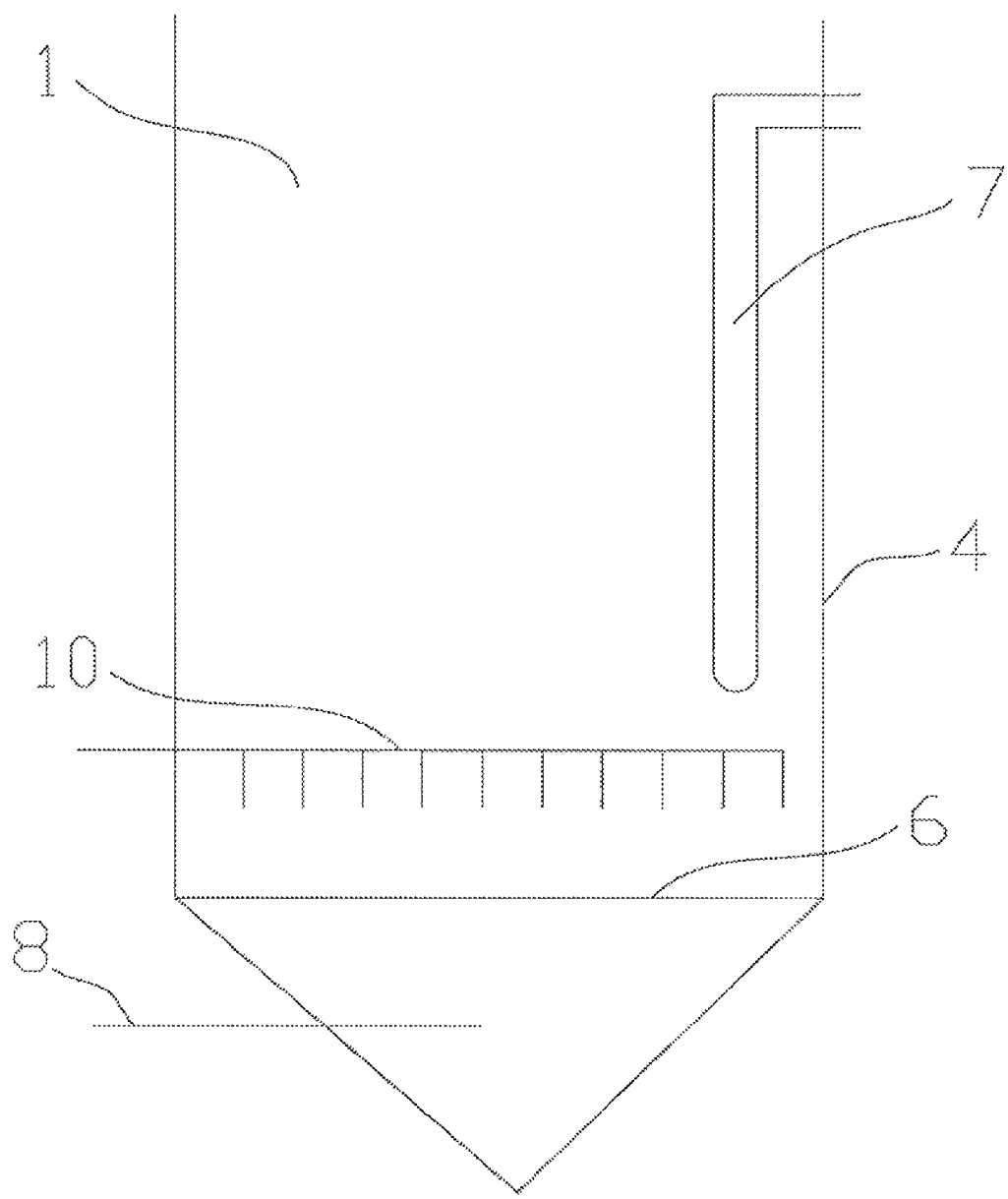

the fluid transport branch pipe passes through the housing of the vessel into the inner cavity.

36 Claims, 11 Drawing Sheets

(58) Field of Classification Search
USPC .......................................................... 261/96
See application file for complete search history.

(56) References Cited

U.S. PATENT DOCUMENTS

| | | |
|---|---|---|
| 5,605,654 A | 2/1997 | Hsieh et al. |
| 8,092,755 B2 | 1/2012 | Castagnos, Jr. et al. |
| 2007/0219393 A1* | 9/2007 | Lin ........................ C07C 51/265 562/410 |

FOREIGN PATENT DOCUMENTS

| | | |
|---|---|---|
| CN | 203955188 U | 11/2014 |
| CN | 204208540 U | 3/2015 |
| CN | 104941523 A | 9/2015 |
| CN | 205182739 U | 4/2016 |
| CN | 106315526 A | 1/2017 |
| CN | 205868196 U | 1/2017 |
| CN | 106492712 A | 3/2017 |
| CN | 207576359 U | 7/2018 |
| JP | 2017512642 A | 5/2017 |
| KR | 20170031046 A | 3/2017 |
| TW | 200916193 A | 4/2009 |
| TW | 201417887 A | 5/2014 |
| TW | I538735 B | 6/2016 |
| WO | 20150153192 A1 | 10/2015 |
| WO | WO-2015153192 A1 * | 10/2015 .............. B01J 19/26 |

* cited by examiner

FLUID DISTRIBUTOR, REACTION DEVICE AND APPLICATION THEREOF

TECHNICAL FIELD

The invention relates to a fluid distributor, in particular to a fluid distributor suitable for transporting a propylene ammonia mixed gas. The invention also relates to a reaction device comprising the fluid distributor and the application of the fluid distributor in fluid transportation or acrylonitrile production.

BACKGROUND

Acrylonitrile is an important chemical raw material of petrochemical industry, and the demand of acrylonitrile in the international market is increasing day by day, so that acrylonitrile production enterprises hope to further expand the capacity. The use of an increased reactor size allows the capacity to be increased without increasing the number of reactor equipment, and relatively, reduces the cost of equipment manufacture, and is therefore considered as a primary means of increasing capacity. It is known that during the production of acrylonitrile, the propylene ammonia fluid distributor is exposed to high temperatures for a long time, and the propylene ammonia mixed gas (hereinafter sometimes referred to as mixed gas) in the fluid distributor is continuously heated by the bed layer during the flow of the head pipe/main pipe/branch pipe (hereinafter sometimes referred to as conduit) of the fluid distributor. As the length of travel of the mixture in the conduit increases, the temperature of the mixture also rises. When the temperature of the mixed gas is higher than the temperature at which ammonia decomposes into active nitrogen atoms (hereinafter, this temperature is sometimes referred to as "nitriding temperature"), a part of ammonia decomposes into active nitrogen atoms and bonds with metal atoms in the conduit due to the continuous presence of free ammonia in the mixed gas to form brittle metal nitride, which is easily embrittled under operating conditions, and can cause the fracture of the fluid distributor, resulting in uneven distribution of ammonia and reduced reactivity, and in severe cases, the reactor is forced to stop for changing the distributor.

U.S. Pat. No. 3,704,690A uses a nitrided resistant alloy to make the distributor, but has proven to be unable to solve the problem of nitriding embrittlement during use by acrylonitrile manufacturing companies, due to certain problems and cost reasons specific to ammonia oxidation. CN1089596A proposes to add a layer of heat insulation on the outer surface of each conduit, so that the temperature of the ammonia-containing mixed gas in the conduit is lower than the nitriding reaction temperature.

DISCLOSURE OF INVENTION

The inventor of the present invention has found through research that even in the case of the size of the conventional reactor, the problem of nitriding and embrittlement of the material of the fluid distributor is caused by the high temperature of the propylene ammonia mixed gas, which causes the local temperature of the fluid distributor to be higher than the nitriding temperature for a long time. If the reactor diameter is further increased, the path length of the mixed gas traveling in the fluid distributor will tend to be further increased, thereby further exacerbating the problem of nitriding embrittlement of the fluid distributor.

The inventors of the present invention have also found that similar problems need to be solved not only in the field of acrylonitrile production but also in the field of transport of other fluids (in particular nitrogen-containing fluids, more particularly ammonia-containing fluids), such as methacrylonitrile production and the like.

The inventors of the present invention have further studied to find a fluid distributor (sometimes referred to as a feed distributor) of a specific structure which exhibits a reduced risk of nitriding embrittlement, and have completed the present invention on the basis thereof.

Specifically, the present invention relates to the following aspects.

1. A fluid distributor adapted to transport a fluid to a vessel inner cavity, the fluid distributor comprising:
one or more (preferably 1-8, more preferably 1-4 or 1-2) fluid transport main pipe(s); either one fluid transport main pipe is configured to form a closed shape (preferably a closed shape substantially conforming to the peripheral contour of the vessel, more preferably a substantially planar closed shape, more preferably a substantially planar circular, elliptical or polygonal shape, more preferably the closed shape is substantially perpendicular to the vessel centerline), when its centerline and/or centerline extension thereof are joined end-to-end; or a plurality of fluid transport main pipes are configured to form a closed shape (preferably a closed shape substantially conforming to the peripheral contour of the vessel, more preferably a substantially planar closed shape, more preferably a substantially planar circular, elliptical or polygonal shape, more preferably the closed shape is substantially perpendicular to the vessel centerline), when their respective centerlines and/or centerline extensions thereof are joined end-to-end, and each of the fluid transport main pipe(s) has at least one (preferably 1-3, more preferably 1) fluid inlet,
a plurality of fluid transport branch pipes (preferably 5-100, more preferably 5-50) disposed on each of said fluid transport main pipes, each of said fluid transport branch pipes having a starting end and a terminal end (said terminal end being in a closed, semi-closed or open configuration, preferably a closed configuration), said starting end being connected to and in fluid communication with said fluid transport main pipe and said starting end and said terminal end defining a length L of said fluid transport branch pipe,
a plurality of open pores (preferably 2-140, more preferably 6-60) disposed along the length of said fluid transport branch pipe in each of said fluid transport branch pipes, a connection portion provided on each of the fluid transport branch pipes (preferably, the connection portion is provided at a position closer to the starting end than the terminal end, and more preferably, the connection portion is provided at a distance from the starting end along the length direction of the fluid transport branch pipe of ¼ or less, ⅙ or less, ⅛ or less, 1/10 or less of the length L of the fluid transport branch pipe), the connection portion being configured to connect (preferably fix, more preferably air-tight fix) the fluid transport branch pipe to the housing (preferably an outer surface of the housing) after the fluid transport branch pipe passes through the housing of the vessel into the inner cavity.

2. The fluid distributor of any of the preceding or subsequent aspects, wherein the inner diameters of the plurality of fluid transport main pipes are identical to or different from (e.g., identical to) each other, and are each independently 150-700 mm (preferably 170-500 mm).

3. The fluid distributor of any of the preceding or subsequent aspects, wherein on each of the fluid transport branch pipes, the plurality of open pores are arranged along the length direction of the fluid transport branch pipe (such as being arranged at equal intervals or unequal intervals, more preferably the distances D1 between any two adjacent open pores are identical to or different from each other, and are respectively and independently 125-375 mm (preferably 175-250 mm)) on the pipe segment (referred to as inner pipe segment) of the fluid transport branch pipe from the connection portion to the terminal end.

4. The fluid distributor of any of the preceding or subsequent aspects, wherein wherein the inner segment of at least one of the fluid transport branch pipes has a constant or varying (e.g., gradually increased or gradually decreased) inner diameter in a direction from the connection portion to the terminal end of the fluid transport branch pipe, and/or the length Li of the inner segment is such that after the fluid transport branch pipe passes through the housing of the vessel and enters the inner cavity, two intersection points are generated between the extension line of the central line of the inner pipe segment towards the head and tail ends of the pipe segment and the inner surface of the housing, and the length of the line segment between the two intersection points is Ld, so that 0<Li<Ld, preferably 0.25Ld≤Li≤0.99Ld, preferably 0.40Ld≤Li<0.99Ld, and more preferably 0.40Ld≤Li<0.50 Ld.

5. The fluid distributor of any of the preceding or subsequent aspects, wherein on each of said fluid transport main pipes, said plurality of fluid transport branch pipes are divided into one or more groups (e.g. multiple groups such as 2 groups or more, particularly 2-8 groups, 2-6 groups, or 2-4 groups), such that in any one group of fluid transport branch pipes, i) the centerlines of any two adjacent fluid transport branch pipes are parallel or substantially parallel to each other along the same direction (referred to as the extension direction of the group of fluid transport branch pipes), and/or, ii) the inner diameters of any two adjacent fluid transport branch pipes are identical to or different from (e.g., identical to) each other, each independently being 50-150 mm (preferably 65-125 mm), and/or, iii) the perpendicular distances D2 of the centerlines of any two adjacent fluid transport branch pipes are identical to or different from (e.g., identical to) each other, each independently being 250-750 mm (preferably 300-650 mm, more preferably 350-550 mm), and/or iv) the D1 and the D2 satisfy the relation: D1/D2≥0.3 (preferably D1/D2≥0.5), and/or, v) the ends of two adjacent fluid transport branch pipes are connected end-to-end to form a line segment having the shape of a fold line or a straight line (preferably, the height difference between the highest point and the lowest point of the fold line is HC, and the length of the longest fluid transport branch pipe in the group of fluid transport branch pipes is Lmax, then HC/Lmax≤44%, preferably HC/Lmax≤37%, more preferably HC/Lmax≤28%, more preferably HC is substantially 0, more preferably the straight line is substantially perpendicular to the extension direction of the group of fluid transport branch pipes), and/or vi) the length of the longest fluid transport branch pipe in the group of fluid transport branch pipes is 5000-29000 mm (preferably 5000-20000 mm, preferably 5000-10000 mm, more preferably 6000-10000 mm.

6. The fluid distributor of any of the preceding or subsequent aspects,
wherein on each of said fluid transport main pipes, said plurality of fluid transport branch pipes is divided into one or more groups (e.g. multiple groups such as 2 groups or more, in particular 2-8 groups, 2-6 groups or 2-4 groups), or all fluid transport branch pipes of said fluid distributor are divided into one or more groups (e.g. multiple groups such as 2 groups or more, in particular 2-8 groups, 2-6 groups or 2-4 groups), then between said groups of fluid transport branch pipes i) the extension directions of one group of fluid transport branch pipes and the other group of fluid transport branch pipes form an angle with each other (preferably are parallel to each other or perpendicular to each other), and/or ii) the projection of one group of fluid transport branch pipes onto said closed shape does not overlap the projection of the other group of fluid transport branch pipes onto said closed shape, preferably, the sum At of the projected areas of all the groups of fluid transport branch pipes contained in the fluid distributor on the closed shape is smaller than the area Ac of the closed shape, preferably At/Ac is 75% or more, more preferably At/Ac is 80% or more, and more preferably At/Ac is 90% or more.

7. The fluid distributor of any of the preceding or subsequent aspects, wherein the centerline of each of the fluid transport branch pipes is a (substantially) straight line.

8. The fluid distributor of any of the preceding or subsequent aspects, wherein the plurality of open pores are identical to or different from (e.g., identical to) each other on each of the fluid transport branch pipes, each independently have a peripheral shape selected from the group consisting of circular, oval, square, rectangular, trapezoidal, and diamond, and/or the plurality of open pores are identical to or different from each other (e.g., the same), each independently have an equivalent circular diameter of 3-10 mm, (preferably 4.5-8.5 mm, more preferably 5.0-7.5 mm).

9. The fluid distributor of any of the preceding or subsequent aspects, wherein on at least one of said fluid transport branch pipes, a fluid flow controller (preferably a fluid flow control valve) is provided on the pipe segment of said fluid transport branch pipe from the connection portion to the starting end (referred to as the outer pipe segment).

10. The fluid distributor of any of the preceding or subsequent aspects, wherein the connection portion is configured to have a shape surrounding the fluid transport branch, preferably a flange shape, or the closed shape has a diameter of 5.5-32.0 meters (preferably 6.0-23.0 meters, more preferably 11.0-23.0 meters or 13.0-23.0 meters).

11. The fluid distributor of any of the preceding or subsequent aspects, further comprising a nozzle disposed surrounding the open pore.

12. The fluid distributor of any of the preceding or subsequent aspects, wherein the vessel is a fluidized bed reactor, the diameter of the inner cavity of the reactor is 5-29 meters (preferably 5-20 meters, more preferably 10-20 meters or 12-20 meters) and the fluid is a nitrogen-containing fluid or an ammonia-containing fluid, in particular a nitrogen-containing gas or an ammonia-containing gas, in particular a mixed gas of alkene and ammonia, more in particular a propylene ammonia mixed gas.

13. A fluid distributor, which is a feeding distributor for uniformly distributing propylene ammonia mixed gas in a fluidized bed reactor, and the feeding distributor comprises:
one or more distributor inlets;
a plurality of branch pipes connected to and in fluid communication with the distributor inlets, respectively, and extending from the distributor inlets toward a reactor interior; an orifice, which orifice provided on the branch pipe; and
nozzles disposed on said branch pipe around and coaxial with said corresponding orifice to distribute the propylene ammonia mixed gas evenly throughout the interior of the reactor, through said distributor inlet, said branch pipe, said orifice and said nozzle.

14. The fluid distributor of any of the preceding or subsequent aspects, wherein the branch pipes adjacent in the extension direction are parallel to each other.
15. The fluid distributor of any of the preceding or subsequent aspects, wherein the distance between the adjacent mutually parallel branched pipes is identical.
16. The fluid distributor of any of the preceding or subsequent aspects, wherein the pore distance between adjacent orifices in the direction of the gas flow is identical.
17. The fluid distributor of any of the preceding or subsequent aspects, wherein a ratio of the pore distance between the adjacent orifices to the vertical distance between the adjacent branch pipes is 1/N, where N is an integer of 2 or more.
18. The fluid distributor of any of the preceding or subsequent aspects, wherein the distance between the adjacent branch pipes is 250 mm and 750 mm.
19. The fluid distributor of any of the preceding or subsequent aspects, wherein the one or more distributor inlets and the plurality of branched pipes are within a same horizontal cross-section of the reactor.
20. The fluid distributor of any of the preceding or subsequent aspects, wherein the length of the branched pipe extending inside the fluidized bed reactor is less than the diameter of the reactor.
21. The fluid distributor of any of the preceding or subsequent aspects, wherein the length of the branched pipe extending inside the fluidized bed reactor is less than the radius of the reactor.
22. The fluid distributor of any of the preceding or subsequent aspects, wherein the fluidized bed reactor has a diameter of 5-29 meters.
23. The fluid distributor of any of the preceding or subsequent aspects, wherein the fluidized bed reactor has a diameter of 5-20 meters.
24. The fluid distributor of any of the preceding or subsequent aspects, wherein the plurality of branched pipes have a pipe diameter of 70-145 mm.
25. The fluid distributor of any of the preceding or subsequent aspects, further comprising one or more feeding main pipes disposed outside the fluidized bed reactor and connected to and in fluid communication with the one or more feed distributor inlets and the plurality of branch pipes, respectively.
26. The fluid distributor of any of the preceding or subsequent aspects, wherein the feeding main pipe is annular, semicircular, or arc-shaped.
27. The fluid distributor of any of the preceding aspects, further comprising a flow controller for controlling the flow of a propylene ammonia mixed gas within the feed distributor.
28. A method of using the fluid distributor of any of the preceding aspects to transport a fluid to a vessel inner cavity, comprising the step of transporting a fluid (preferably a gas, more preferably the propylene ammonia mixed gas) to the at least one fluid inlet of the fluid distributor, the fluid passing into the inner cavity through at least the fluid transport main pipe, the fluid transport branch pipes and the open pores.
29. Use of a fluid distributor as described in any of the preceding aspects as a feed distributor for feeding a reaction feedstock, preferably a propylene ammonia mixed gas, to the inner cavity of an ammoxidation reactor.
30. A reaction apparatus comprising a reactor and the fluid distributor of any of the preceding aspects, wherein the reactor has at least a housing, a plurality of through-holes provided in the housing, and an inner cavity defined by an inner surface of the housing, the through-holes having a one-to-one correspondence relationship in number and arrangement positions with fluid transport branch pipes of the fluid distributor, whereby each fluid transport branch pipe can enter the inner cavity through one through-hole corresponding thereto, and the fluid transport branch pipe is airtightly fixed to the outer surface of the housing through a connection portion of the fluid transport branch pipe after passing through the through-hole.
31. A process for producing acrylonitrile, comprising the steps of feeding a propylene ammonia mixed gas into a reactor (preferably a fluidized bed reactor) inner cavity and feeding an oxygen-containing gas (preferably air) into the reactor inner cavity by using the fluid distributor according to any of the preceding aspects or the process according to any of the preceding aspects, or subjecting propylene to an ammoxidation reaction in the reactor of any of the preceding aspects to produce acrylonitrile.

Technical Effects

According to the fluid distributor of the invention, at least one of the following technical effects can be realized:
(1) the reactor can meet the requirement of uniform distribution of fluid (particularly propylene ammonia mixed gas) not only in the reactor of the existing size, but also in the reactor with a larger size.
(2) In particular in the case of the transport of nitrogen-containing fluids or ammonia-containing fluids, such as a propylene ammonia mixed gas, it is possible to present a reduced risk of nitriding embrittlement not only in reactors of the existing size, but also even in reactors of a larger size.

DRAWINGS

Figure 2:
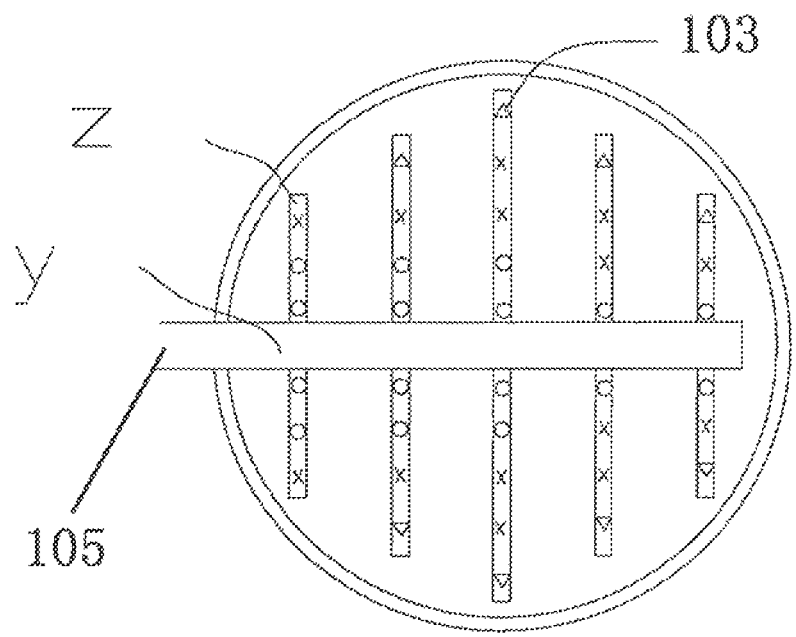
Figure 3A:
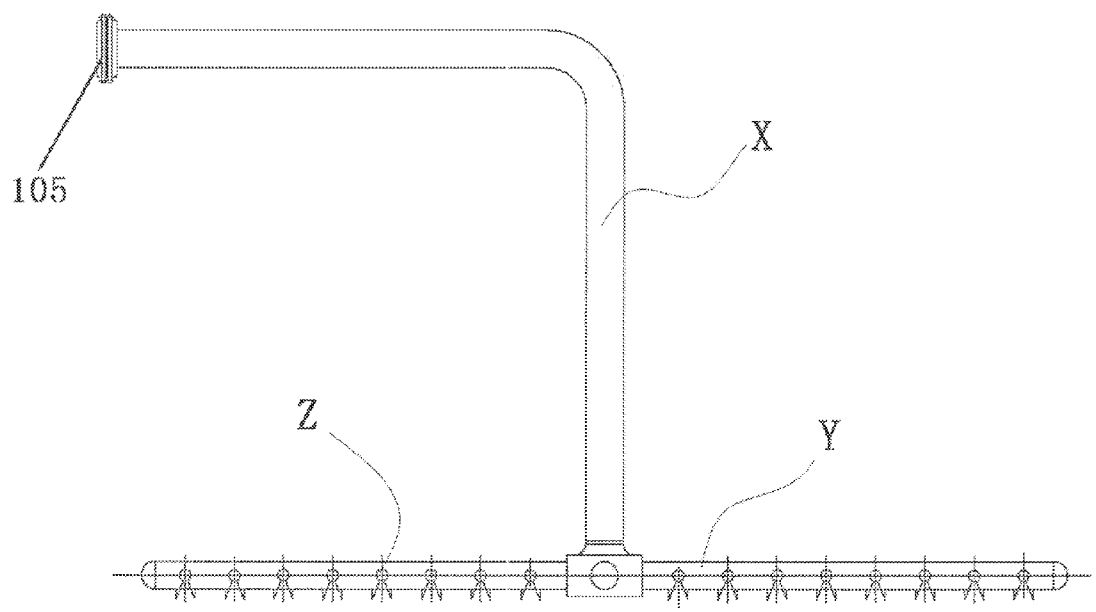
Figure 3B:
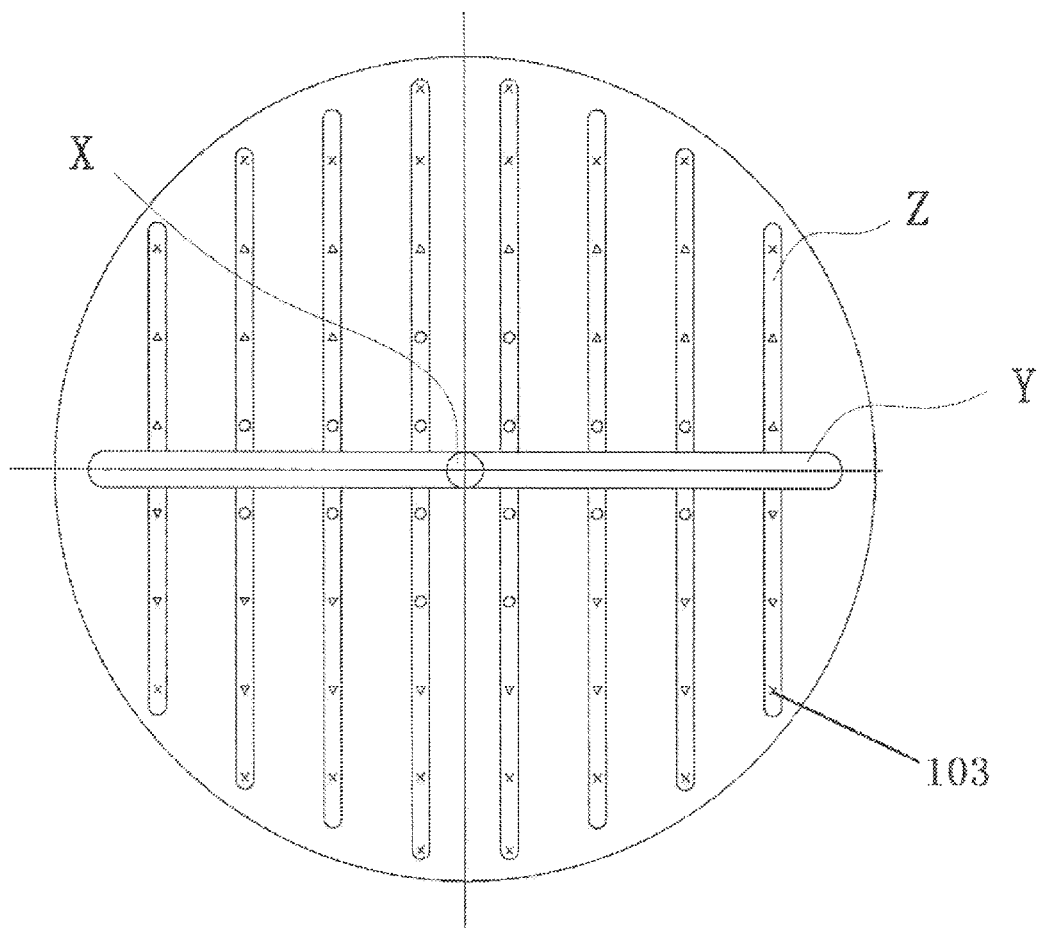
Figure 4:
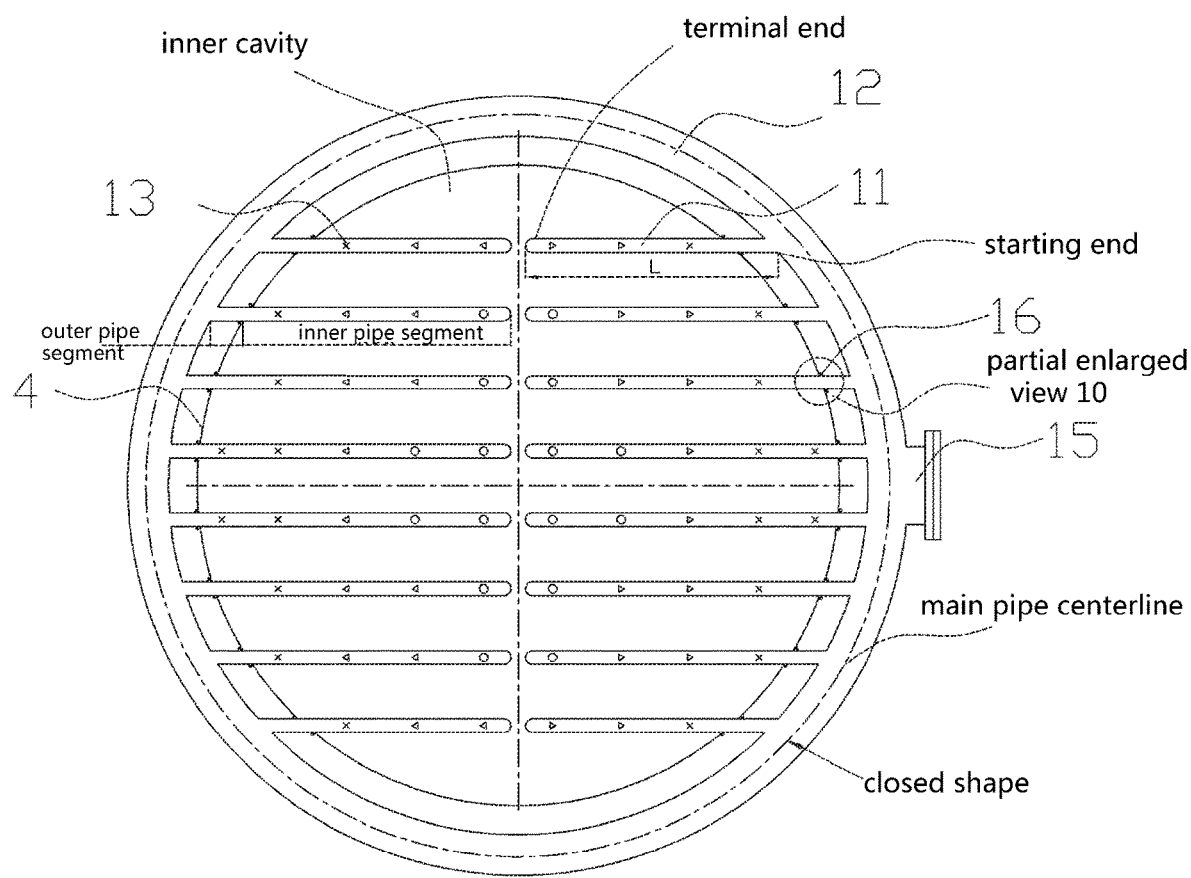
Figure 5:
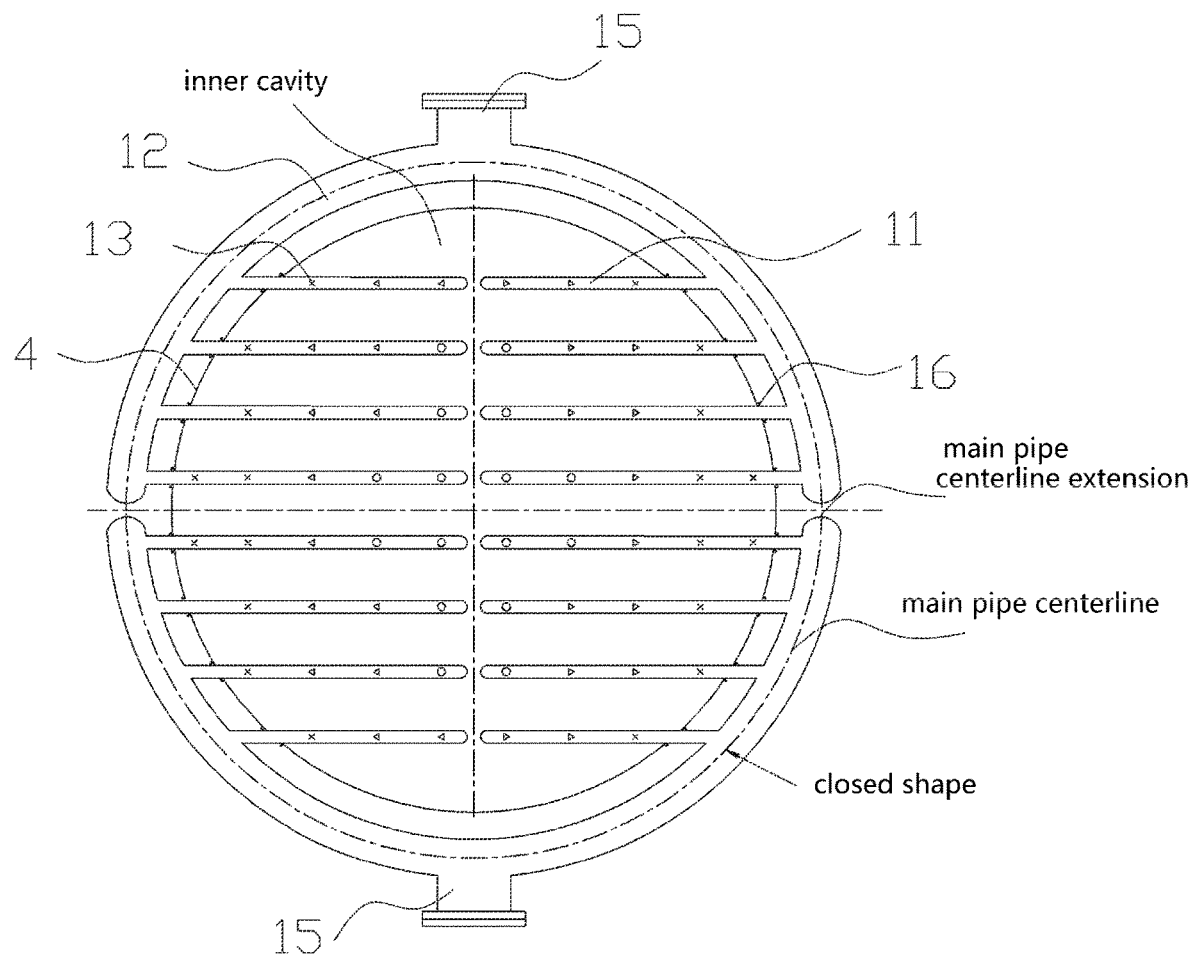
Figure 6:
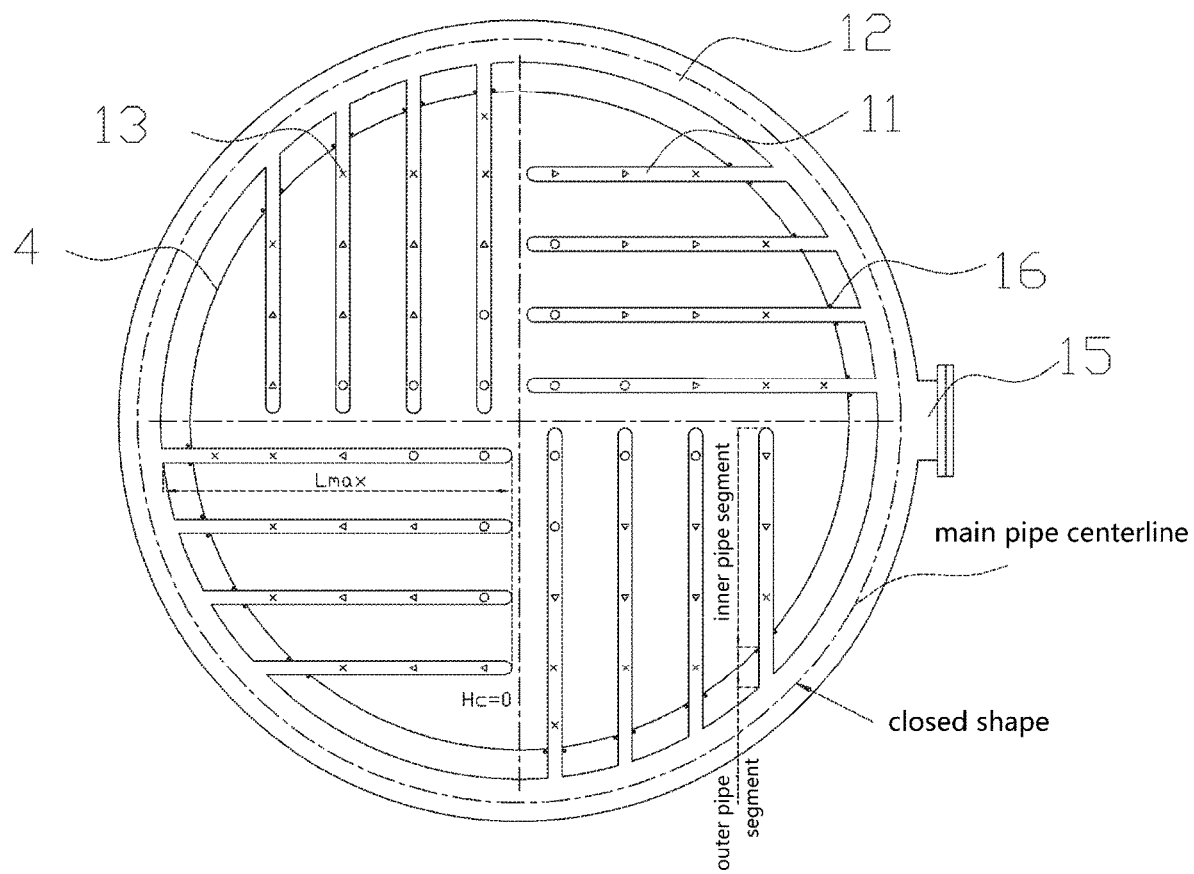
Figure 7:
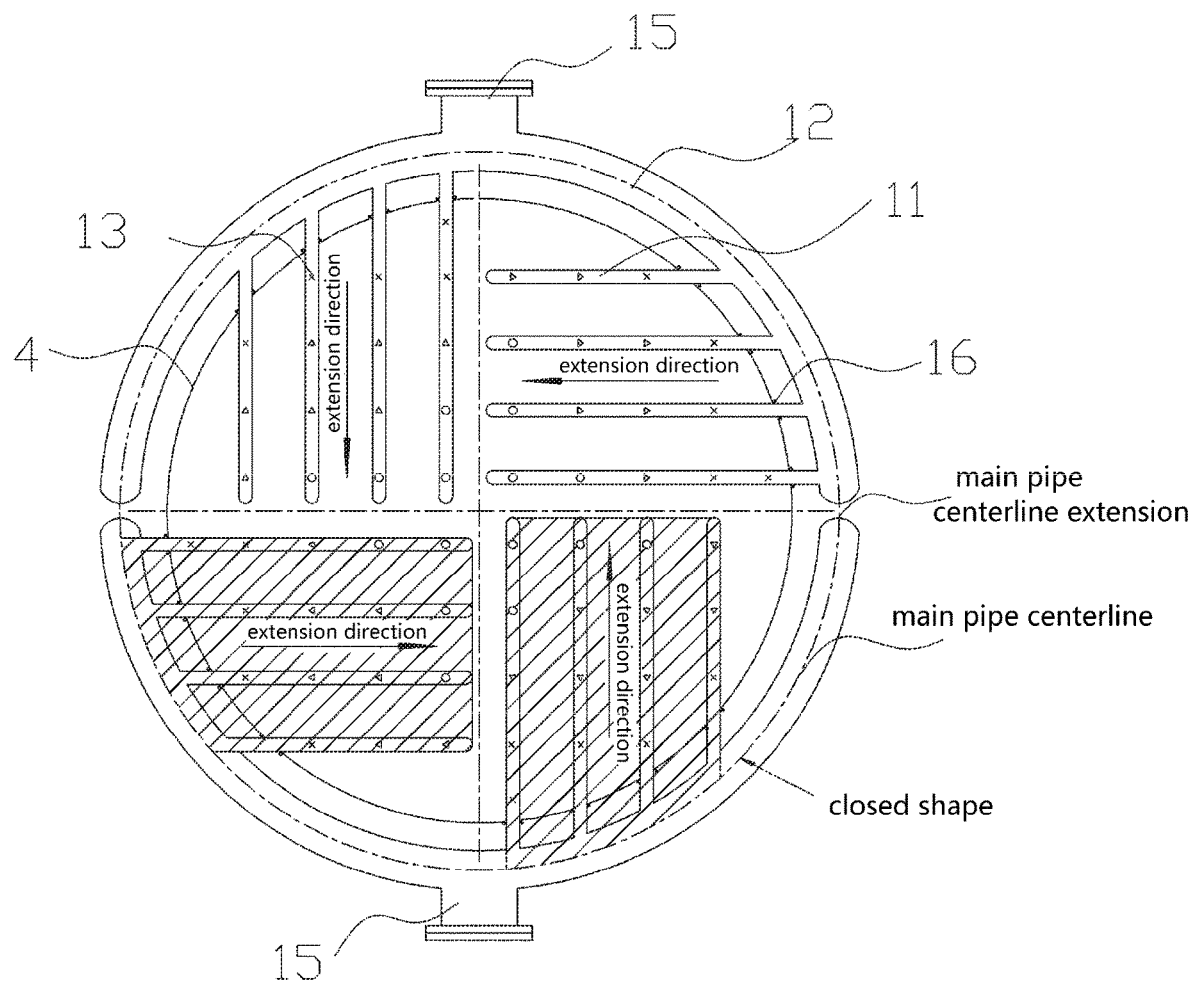
Figure 8:
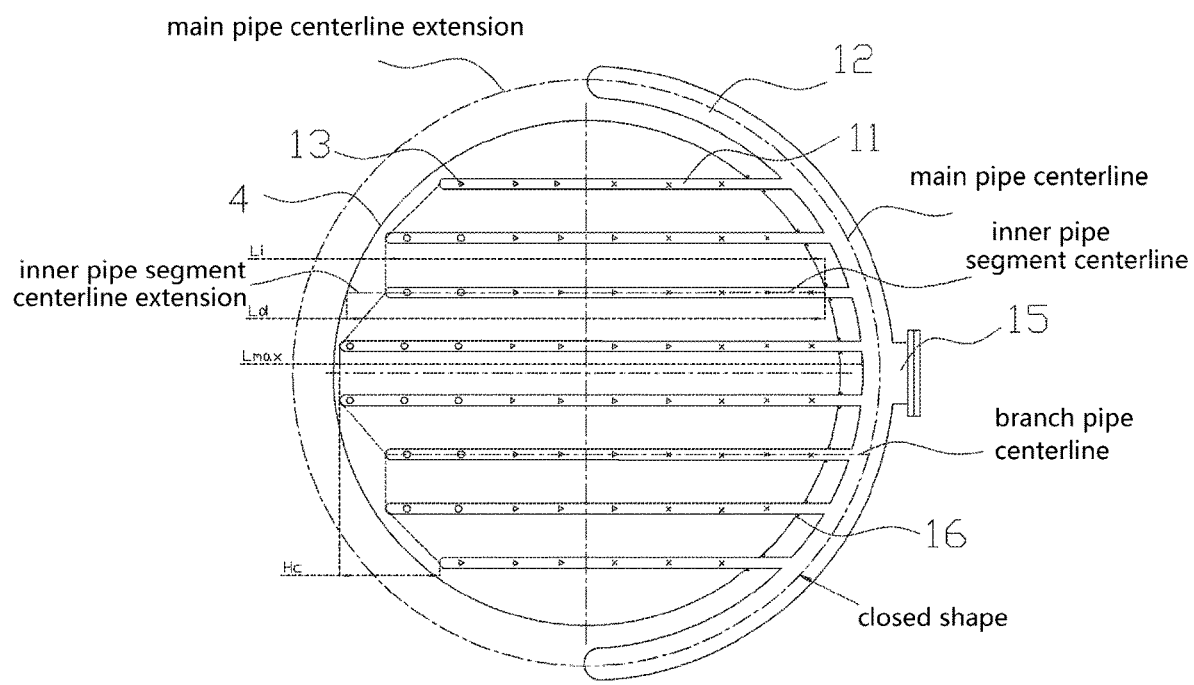
Figure 9:
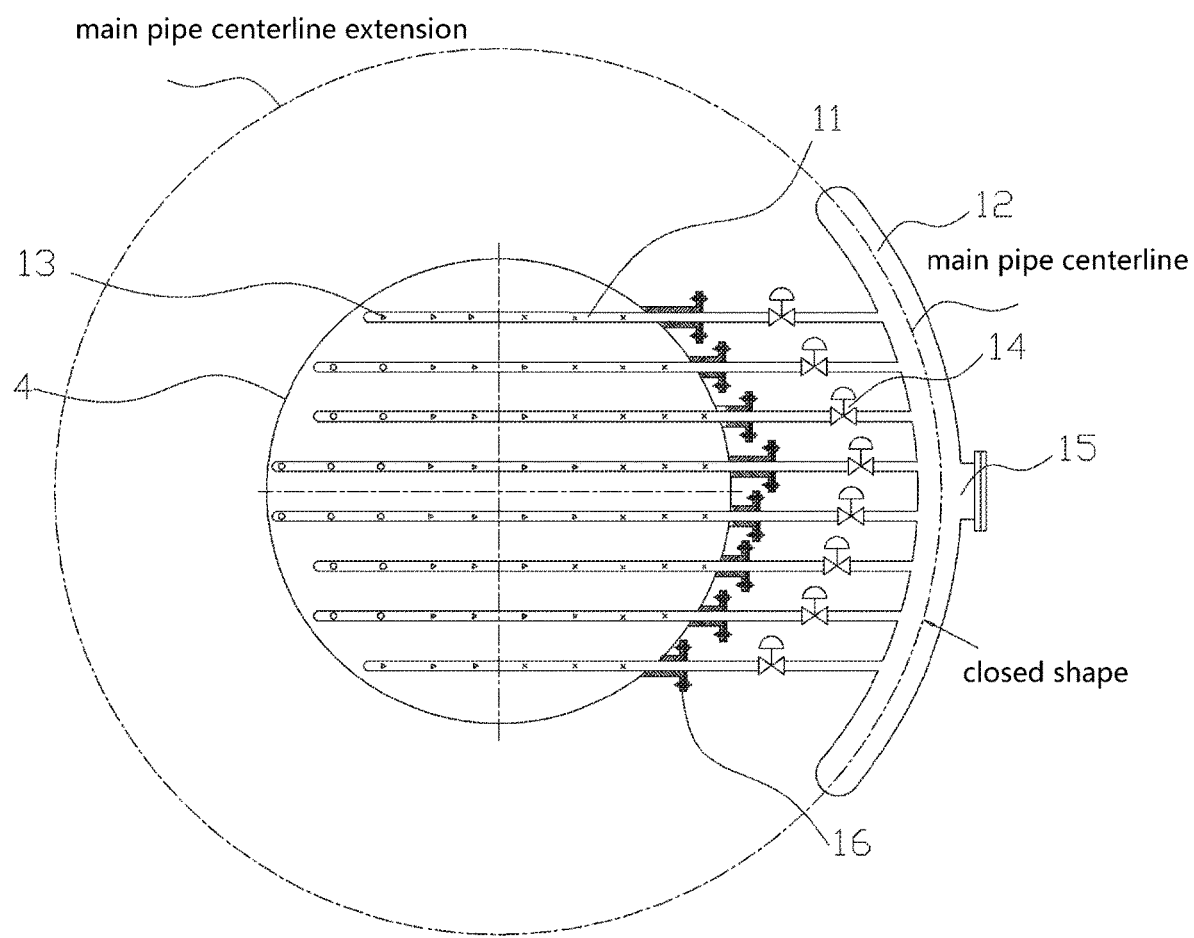
Figure 10:
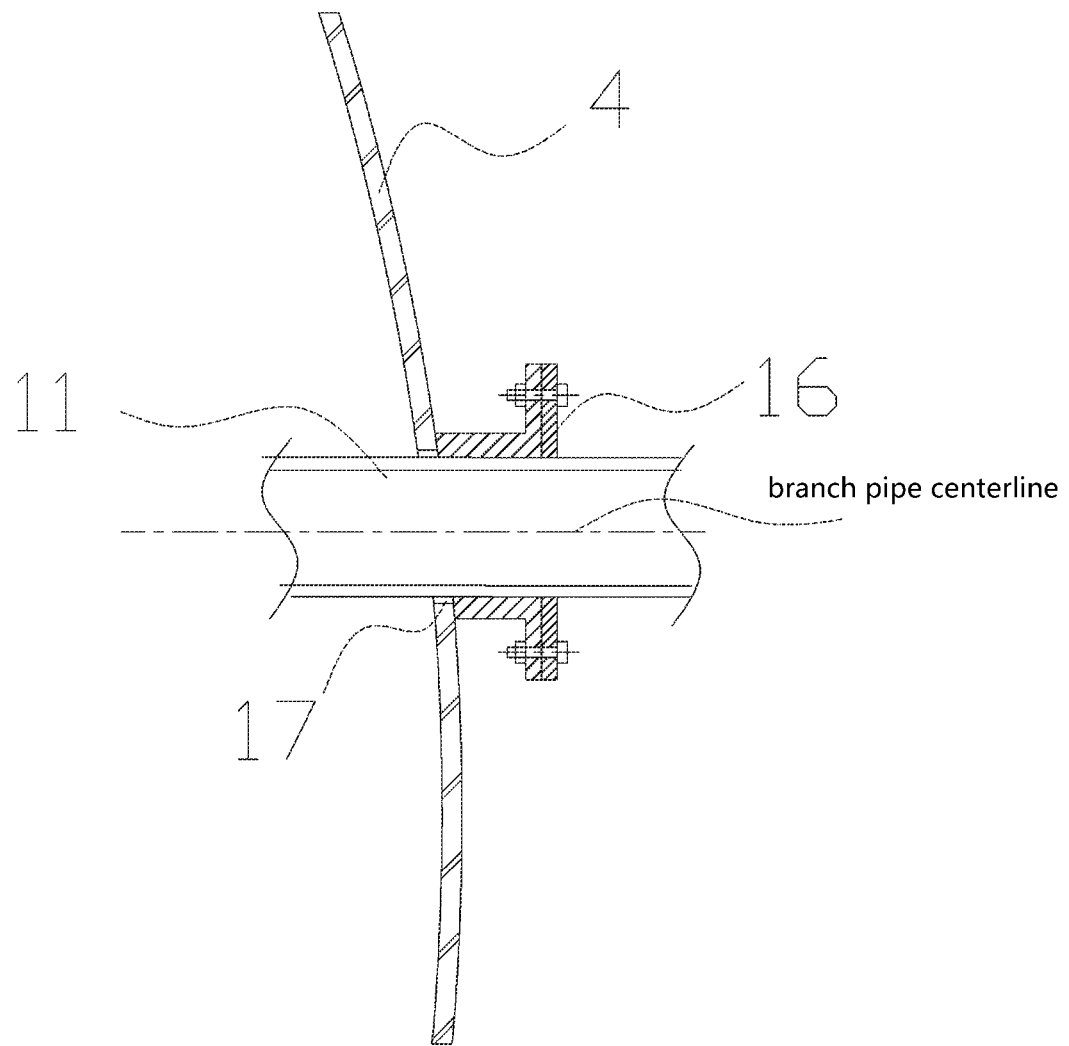

FIG. 1 is a schematic structural view of a prior art fluidized bed reactor for the ammoxidation of propylene.
FIG. 2 is a schematic structural view of one embodiment of a prior art fluid distributor.
FIGS. 3A and 3B are a schematic structural view of another embodiment of a prior art fluid distributor, wherein FIG. 3A is a side view and FIG. 3B is a bottom view.
FIG. 4 is a schematic structural view of one embodiment of the fluid distributor of the present invention.
FIG. 5 is a schematic structural view of one embodiment of the fluid distributor of the present invention.
FIG. 6 is a schematic structural view of one embodiment of the fluid distributor of the present invention.
FIG. 7 is a schematic structural view of one embodiment of the fluid distributor of the present invention.
FIG. 8 is a schematic structural view of one embodiment of the fluid distributor of the present invention.
FIG. 9 is a schematic structural view of one embodiment of the fluid distributor of the present invention.
FIG. 10 is an enlarged partial schematic view of FIG. 4, illustrating the attachment of the fluid transport branch pipe to the housing.

DESCRIPTION OF THE REFERENCE NUMERALS

1: Propylene ammoxidation reactor
13 and 103: Open pore
4: Housing
15 and 105: Fluid inlet
6: Air distribution plate
7: Cooling coil
8: Process air intake 10 and 100: Fluid distributor
x: Head pipe
y: Main pipe
z: Branch pipe
11: Fluid transport branch pipe (sometimes called branch pipe for short)
12: Fluid transport main pipe (sometimes also referred to as a feeding main pipe)
14: Fluid flow controller
16: Connection portion
17: Through-hole

DETAILED DESCRIPTION

Reference will now be made in detail to the present embodiments of the present invention, but it should be understood that the scope of the invention is not limited by the embodiments, but is defined by the appended claims.

All publications, patent applications, patents, and other references mentioned in this specification are herein incorporated by reference in their entirety. Unless defined otherwise, all technical and scientific terms used herein have the same meaning as commonly understood by one of ordinary skill in the art to which this invention belongs. In case of conflict, the present specification, including definitions, will control.

When the specification derives materials, substances, methods, procedures, means, or components, or the like with the expressions such as "known to one of ordinary skill in the art", "prior art", or the like, it is intended that the subject matter so derived encompass not only those materials, substances, methods, procedures, means, or components which have been conventionally used in the art at the time of filing this application, but also those which may not be so commonly used at the present time, but will become known in the art as being suitable for a similar purpose.

In the context of the present invention, the term "fluid" refers to any substance that behaves as a liquid or as a gas at 25° C. and one standard atmospheric pressure. Specific examples of the fluid include a nitrogen-containing fluid or an ammonia-containing fluid, particularly a nitrogen-containing gas or an ammonia-containing gas, particularly an mixed gas of ammonia and olefins (e.g., C2-6 olefins), and more particularly a propylene ammonia mixed gas. In particular, the content of ammonia in the fluid is not particularly limited, and the skilled person can arbitrarily select it according to the circumstances.

All percentages, parts, ratios, etc. referred to in this specification are on a molar basis and the reaction pressures are gauge pressures unless otherwise specifically indicated. In the context of this specification, any two or more embodiments of the invention may be combined in any combination, and the resulting solution is part of the original disclosure of this specification, and is within the scope of the invention.

According to an embodiment of the present invention, a fluid distributor is provided. The fluid distributor is adapted to transport a fluid to the inner cavity of the vessel.

According to an embodiment of the present invention, the fluid is a nitrogen-containing fluid or an ammonia-containing fluid, in particular a nitrogen-containing gas or an ammonia-containing gas, in particular a mixed gas of alkene and ammonia, more in particular a propylene ammonia mixed gas.

According to an embodiment of the present invention, the fluid distributor comprises at least one or more fluid transport main pipes.

According to an embodiment of the present invention, when one of said fluid transport main pipes is present, said fluid transport main pipe is configured to form a closed shape when its centerline and/or centerline extension is connected end to end. In addition, when a plurality of the fluid transport main pipes are present, the fluid transport main pipes are configured to form a closed shape when the centerlines and/or centerline extensions thereof are connected end to end.

In the context of the present invention, by "centerline extension" is meant that the centerline is replaced by its centerline extension when the fluid transport main pipe is discontinuous or broken. Other concepts may be similarly understood.

According to an embodiment of the present invention, as the closed shape, a closed shape substantially conforming to the contour of the outer periphery of the vessel is preferred, more preferably a substantially planar closed shape, more preferably a substantially planar circular, elliptical or polygonal shape. According to an embodiment of the present invention, the closed shape is substantially perpendicular to a center line of the vessel. In other words, the closed shape is substantially planar and the closed shape is substantially parallel to the cross-section of the vessel.

For clarity of illustration, FIGS. 4, 5, 7, and 8 illustrate what the centerline, centerline extension, and closed shape (all circular) of the fluid transport main pipe are, all shown in dashed lines, but the invention is not limited to these particular shapes. Moreover, the peripheral outline of the vessel is the shape of the housing 4. FIGS. 4 and 5 also illustrate what is an inner cavity, i.e. the inner space enclosed by the housing 4.

In the context of the present invention, by "substantially" is meant allowing for deviations that are acceptable or reasonably recognized by those skilled in the art. According to an embodiment of the present invention, the diameter of the closed shape, such as the equivalent circular diameter, is typically 5.5-32.0 meters, preferably 6.0-23.0 meters, more preferably 11.0-23.0 meters or 13.0-23.0 meters.

According to an embodiment of the present invention, each of said fluid transport main pipes has at least one fluid inlet. Preferably, each of said fluid transport main pipe has 1-3 or 1 fluid inlet.

According to an embodiment of the present invention, a plurality of fluid transport branch pipes are provided on each of said fluid transport main pipe. By way of example, the number of fluid transport branch pipes may be 5-100 or 5-50, although the invention is not limited thereto.

According to an embodiment of the present invention, each of the fluid transport branch pipes has a starting end and a terminal end. By way of example, the terminal ends may be closed, semi-closed or open structures, with closed structures being preferred. Additionally, the starting end is connected to and in fluid communication with the fluid transport main pipe, and the starting end and the terminal end define a length L of the fluid transport branch pipe.

For clarity, FIG. 4 illustrates what are the starting end and the terminal end of the fluid transport branch pipes, and how the length L is determined.

According to an embodiment of the present invention, a plurality of open pores (also referred to as orifices) are provided in each of the fluid transport branch pipes along the length of the fluid transport branch pipe. The number of the open pores may be, for example, 2 to 140 or 6 to 60, but the present invention is not limited thereto.

According to an embodiment of the present invention, a connection portion is provided on each of the fluid transport branch pipes. Furthermore, the connection portion is configured to connect (preferably fix, more preferably air-tight fix) the fluid transport branch pipe to the housing (preferably an outer surface of the housing) after the fluid transport branch pipe passes through the housing of the vessel into the inner cavity. For example, the fluid transport branch can be fixed (preferably hermetically fixed) on the housing, in particular on the outer surface of the housing.

According to an embodiment of the present invention, the connection portion is disposed closer to the starting end than to the terminal end. Alternatively, the distance between the disposition position of the connection portion and the starting end along the length direction of the fluid transport branch pipe is less than or equal to ¼, less than or equal to ⅙, less than or equal to ⅛, less than or equal to 1/10 or less of the length L of the fluid transport branch pipe.

According to an embodiment of the present invention, the fluid transport main pipe is one or more, preferably 1-8, more preferably 1-4 or 1-2.

According to an embodiment of the present invention, when there are a plurality of the fluid transport main pipes, the inner diameters of the fluid transport main pipes are identical to or different from (e.g., identical to) each other, and are respectively 150-700 mm, preferably 170-500 mm.

According to an embodiment of the present invention, on each of the fluid transport branch pipes, the plurality of open pores are arranged on a pipe segment (referred to as an inner pipe segment) of the fluid transport branch pipe from the connection portion to the terminal end along the length direction of the fluid transport branch pipe.

For clarity of illustration, FIGS. 4 and 6 illustrate how the inner and outer pipe segments are determined.

According to an embodiment of the present invention, the plurality of open pores may be equally or unequally spaced. Preferably, the distances D1 between any two adjacent open pores are identical to or different from each other, and are 125-375 mm, preferably 175-250 mm.

According to an embodiment of the present invention, the inner pipe segment of at least one of said fluid transport branch pipes has a constant or varying inner diameter in a direction from the connection portion to the terminal end of said fluid transport branch pipe. Examples of the varying include a gradual increase and a gradual decrease.

According to an embodiment of the present invention, the length Li of the inner pipe segment is such that after the fluid transport branch pipe passes through the housing of the vessel and enters the inner cavity, two intersection points are generated between the extension line of the central line of the inner pipe segment towards the head and tail ends of the pipe segment and the inner surface of the housing, and the length of the line segment between the two intersection points is Ld, so that $0<Li<Ld$, preferably $0.25Ld \le Li \le 0.99Ld$, preferably $0.40Ld \le Li < 0.99Ld$, and more preferably $0.40Ld \le Li < 0.50\ Ld$.

For the sake of clarity, FIG. 8 illustrates how the centerline, the extension, Li and Ld of the inner pipe segments are determined, and also how the centerline of the branch pipe is determined.

According to an embodiment of the present invention, on each of the fluid transport main pipes, the plurality of fluid transport branch pipes are divided into one or more groups, such as 2 groups or more, in particular 2-8 groups, 2-6 groups or 2-4 groups, and then in any one group of fluid transport branch pipes, the centerlines of any two adjacent fluid transport branch pipes are parallel or substantially parallel to each other along the same direction (which is referred to as the extension direction of the group of fluid transport branch pipes in the context of the present invention). For clarity of explanation, FIG. 7 illustrates the (four) extension directions, which are respectively indicated by four arrows, but the present invention is not limited to the four extension directions.

According to an embodiment of the present invention, on each of the fluid transport main pipes, the plurality of fluid transport branch pipes are divided into one or more groups, such as 2 groups or more, in particular 2-8 groups, 2-6 groups or 2-4 groups, and in any one group of fluid transport branch pipes, the inner diameters of any two adjacent fluid transport branch pipes are identical to or different from (e.g., identical to) each other, and are each independently 50-150 mm, preferably 65-125 mm. According to an embodiment of the present invention, the plurality of fluid transport branch pipes are divided into one or more groups, such as 2 groups or more, particularly 2-8 groups, 2-6 groups or 2-4 groups, on each of the fluid transport main pipes, and in any one group of fluid transport branch pipes, the vertical distances D2 of the centerlines of any two adjacent fluid transport branch pipes are the same or different (e.g., identical), and are respectively 250-750 mm, preferably 300-650 mm, more preferably 350-550 mm.

According to an embodiment of the present invention, on each of the fluid transport main pipes, the plurality of fluid transport branch pipes are divided into one or more groups, such as 2 groups or more, particularly 2-8 groups, 2-6 groups or 2-4 groups, and in any one group of fluid transport branch pipes, the relationship between D1 and D2 is satisfied: $D1/D2 \ge 0.3$, preferably $D1/D2 \ge 0.5$.

According to an embodiment of the present invention, on each of the fluid transport main pipes, the plurality of fluid transport branch pipes are divided into one or more groups, such as 2 groups or more, particularly 2-8 groups, 2-6 groups or 2-4 groups, and in any one group of fluid transport branch pipes, the ends of two adjacent fluid transport branch pipes are connected end-to-end to form a line segment. Generally, the line segments have the shape of fold lines or straight lines.

According to an embodiment of the present invention, assuming that the height difference between the highest and the lowest point of the fold line is HC, and the length of the longest fluid transport branch pipe of the group of fluid transport branch pipes is Lmax, $HC/Lmax \le 44\%$, preferably $HC/Lmax \le 37\%$, more preferably $HC/Lmax \le 28\%$, more preferably HC is substantially 0, more preferably the straight line is substantially perpendicular to the extension direction of the group of fluid transport branch pipes.

For clarity of illustration, FIG. 6 illustrates the segments in a straight line shape and FIG. 8 illustrates the segments in a fold line shape, but the invention is not limited to these particular shapes. In addition, these figures also illustrate how HC and Lmax are determined.

According to an embodiment of the present invention, on each of the fluid transport main pipes, the plurality of fluid transport branch pipes are divided into one or more groups, such as 2 groups or more, particularly 2-8 groups, 2-6 groups or 2-4 groups, then in any group of fluid transport branch pipes, the length Lmax of the longest fluid transport branch pipe in the group of fluid transport branch pipes is 5000-29000 mm, preferably 5000-20000 mm, preferably 5000-10000 mm, more preferably 6000-10000 mm.

According to an embodiment of the present invention, on each of the fluid transport main pipes, the plurality of fluid transport branch pipes are divided into one or more groups, or all the fluid transport branch pipes of the fluid distributor are divided into one or more groups, such as 2 groups or more, especially 2-8 groups, 2-6 groups or 2-4 groups, then between the fluid transport branch pipes of the plurality of groups, the extension directions of the fluid transport branch pipes of one group and the fluid transport branch pipes of the other group form an angle with each other, preferably are parallel with each other or are perpendicular with each other, including substantially parallel or substantially perpendicular.

According to an embodiment of the present invention, on each of the fluid transport main pipes, the plurality of fluid transport branch pipes are divided into one or more groups, or all fluid transport branch pipes of the fluid distributor are divided into one or more groups, such as 2 groups or more, especially 2-8 groups, 2-6 groups or 2-4 groups, then between the plurality of groups of fluid transport branch pipes, the projection of one group of fluid transport branch pipes on the closed shape is not overlapped with the projection of another group of fluid transport branch pipes on the closed shape. Preferably, the sum At of the projected areas of all the groups of fluid transport branch pipes contained in the fluid distributor on the closed shape is smaller than the area Ac of the closed shape, preferably At/Ac is 75% or more, more preferably At/Ac is 80% or more, and more preferably At/Ac is 90% or more.

For clarity of illustration, FIG. 7 illustrates how the projections are determined. In FIG. 7, 2 projections, each represented by a 2-block shaded area, are illustrated, but the present invention is not limited to the 2 projections. As illustrated in this Figure, the projection is actually a projection on the closed shape of a figure defined by a line segment formed by connecting the ends of all the fluid transport branch pipes in each group of fluid transport branch pipes end-to-end, a center line of the fluid transport main pipe where the line segment is located (as the case may be, a centerline extension is also included), and outer edges of the two outermost fluid transport branch pipes in the group of fluid transport branch pipes in the length direction. In general, the figure and the closed shape are both substantially planar shapes, and both are typically in substantially the same plane.

According to an embodiment of the present invention, when all the fluid transport branch pipes of the fluid distributor are divided into a plurality of groups, the fluid transport branch pipes of each group may all be located on the same fluid transport main pipe, or may be located on different fluid transport main pipes respectively or in any combination with each other, and in particular may be located on different fluid transport main pipes respectively or in any combination with each other. Here, "in any combination with each other" means that when the number of groups of fluid transport branch pipes is different from the number of fluid transport main pipes, 1 or more groups of fluid transport branch pipes are on the same fluid transport main pipe, and the remaining groups of fluid transport branch pipes are on the remaining one or more fluid transport main pipes. As a specific example, assuming that there are 4 sets of fluid transport branch pipes and 2 fluid transport main pipe, 1 set of fluid transport branch pipes among the 4 sets of fluid transport branch pipes is on one fluid transport main pipe, and the other 3 sets of fluid transport branch pipes are on the other fluid transport main pipe, or 2 sets of fluid transport branch pipes among the 4 sets of fluid transport branch pipes are on one fluid transport main pipe, and the other 2 sets of fluid transport branch pipes are on the other fluid transport main pipe, as any combination with each other.

According to an embodiment of the present invention, the center line of each of said fluid transport branch pipes is substantially straight. That is, each of the fluid transport branch pipes is substantially a straight pipe.

According to an embodiment of the present invention, the plurality of open pores in each of the fluid transport branch pipes are identical to or different from (e.g., identical to) one another, and each independently have a peripheral shape selected from the group consisting of circular, oval, square, rectangular, trapezoidal, and diamond. According to an embodiment of the present invention, a fluid flow controller, preferably a fluid flow control valve, is arranged on at least one of the fluid transport branch pipes on the pipe segment of the fluid transport branch pipe from the connection portion to the starting end (referred to as outer pipe segment).

According to an embodiment of the present invention, the connection portion is configured to have a shape surrounding the fluid transport branch pipe, preferably a flange shape.

According to an embodiment of the present invention, the fluid distributor further comprises a nozzle disposed surrounding the open pore. With this arrangement, the branch pipe is in fluid communication with the respective nozzle through the open pore, resulting in that the transport fluid exiting the open pore is rectified by the nozzle and then enters the inner cavity of the vessel through an opening (generally circular) at the other end of the nozzle.

According to an embodiment of the present invention, the open pores are coaxial with their respective nozzles and are located on a radial cross-section perpendicular to the centerline of the respective branch pipe.

According to an embodiment of the present invention, the plurality of open pores are identical to or different from (e.g., identical to) each other, each independently having a diameter (generally equivalent circular diameter) of 3-10 mm (preferably 4.5-8.5 mm, more preferably 5.0-7.5) at each of the fluid transport branch pipes. Preferably, the diameter of the open pore is smaller than the diameter of the respective nozzle and nozzle tip opening. In addition, the diameters of the open pores may be identical to or different from each other along the length of the fluid transport branch pipe, for example the gradually increasing or gradually decreasing diameters.

According to an embodiment of the present invention, the nozzles extend downwards from the branch pipe. Further, the extension angles of the nozzles may be identical or different. Preferably, the tips of all nozzles are in substantially the same horizontal cross-section.

According to an embodiment of the present invention, the nozzle may be selected from cylindrical, conical, and/or, preferably, cylindrical. In addition, the cross-sections of the nozzles each independently have a shape selected from the group consisting of circular, oval, square, rectangular, trapezoidal, and diamond, preferably circular and/or oval, more preferably circular.

According to an embodiment of the present invention, the ratio of the column length of the nozzle to the inner diameter of the nozzle is 4 or more, preferably 6 or more, and more preferably 8 or more.

According to an embodiment of the present invention, in the case of a fluidized bed reactor for propylene ammoxidation, the vertical distances from the tips of all the nozzles to the air distribution plate below are substantially identical.

According to an embodiment of the present invention, the vessel is a fluidized bed reactor. Generally, the diameter of the inner cavity of the reactor is 5 to 29 meters, preferably 5 to 20 meters, more preferably 10 to 20 meters or 12 to 20 meters. The inventor finds through a great deal of experiments, calculations and computer simulations that the fluid distributor can meet the requirement of a propylene ammoxidation fluidized bed reactor with the inner cavity diameter, namely, the temperature of the mixed gas in the fluid distributor is ensured to be always lower than the nitriding temperature.

According to an embodiment of the present invention, the fluid distributor is a feed distributor for uniformly distributing a propylene ammonia mixed gas inside a fluidized bed reactor, the feed distributor comprising:
one or more distributor inlets (i.e., the fluid inlet);
a plurality of transport branch pipes (i.e., the fluid transport branch pipes) that are respectively connected to and respectively in fluid communication with the distributor inlets, and that extend from the distributor inlets toward the interior of the reactor; the open pores, which open pores are arranged on the transport branch pipe; and nozzles disposed on the transport branch pipes around the respective open pores and coaxial with the respective open pores so that the propylene ammonia mixed gas passes through the distributor inlet, the transport branch pipes, the open pores and the nozzles and is finally uniformly distributed inside the reactor,
one or more feeding main pipes (i.e. the fluid transport main pipe) disposed outside the fluidized bed reactor and respectively connected to and in fluid communication with the one or more distributor inlets and the plurality of transport branch pipes.

According to an embodiment of the present invention, the present invention further relates to a method for transporting a fluid to a inner cavity of a container using the fluid distributor of the present invention (hereinafter referred to as fluid transport method). The method includes the step of transporting a fluid to the at least one fluid inlet of the fluid distributor into the inner cavity through at least the fluid transport main pipe, the fluid transport branch pipe and the open pores. Here, the fluid is preferably a gas, and more preferably a propylene ammonia mixed gas. In addition, as the vessel, a fluidized bed reactor is preferable.

According to an embodiment of the present invention, the invention also relates to the use of the fluid distributor according to the invention as a feed distributor for feeding reaction raw materials into the inner cavity of an ammonia oxidation reactor. Here, as the reaction raw material, it is preferably a propylene ammonia mixed gas.

According to an embodiment of the present invention, the invention also relates to a reaction apparatus. The reactor apparatus comprises a reactor and a fluid distributor according to the invention as described above.

According to an embodiment of the present invention, the reactor has at least a housing, a plurality of through-holes provided on the housing, and an inner cavity defined by an inner surface of the housing. And the through-holes are in one-to-one correspondence relationship with the fluid transport branch pipes of the fluid distributor in number and arrangement positions, so that each fluid transport branch pipe can pass through one through-hole corresponding thereto to enter the inner cavity, and the fluid transport branch pipes are fixed on the outer surface of the housing in an airtight manner through the connection portions of the fluid transport branch pipes after passing through the through-holes.

According to an embodiment of the present invention, the present invention further relates to a method for producing acrylonitrile, comprising the steps of using the fluid distributor according to the present invention as described above to feed a propylene ammonia mixed gas into a reactor (such as a fluidized bed reactor) inner cavity and to feed an oxygen-containing gas into the reactor inner cavity, thereby subjecting propylene to ammoxidation to produce acrylonitrile. Here, as the oxygen-containing gas, air may be specifically mentioned.

According to an embodiment of the present invention, the present invention further relates to a method for producing acrylonitrile, comprising the steps of using the fluid transportation method of the present invention as described above to transport a propylene ammonia mixed gas into a reactor (such as a fluidized bed reactor) inner cavity and transport an oxygen-containing gas into the reactor inner cavity, thereby subjecting propylene to ammoxidation to produce acrylonitrile. Here, as the oxygen-containing gas, air may be specifically mentioned.

According to an embodiment of the present invention, there is also provided a process for producing acrylonitrile, comprising the step of subjecting propylene to an ammoxidation reaction in the reactor apparatus according to the above aspect of the present invention to produce acrylonitrile.

According to an embodiment of the present invention, the length of the branch pipes of the same type of fluid distributor is correspondingly increased when the diameter of the reactor is increased, so that the temperature rise of the mixed gas stream after passing through the conduit is greater. When nozzles are present, the mass flow of the mixture in the branch pipe is the product of the number of nozzles and the mass flow of the mixture exiting the individual nozzles. Assuming that the nozzle distance and the mass flow of the mixture through the individual nozzles are the same, the mass flow of the propylene ammonia mixed gas through the longest branch will increase accordingly. In the case where the pipe diameter of the branch pipe is relatively fixed, a slight decrease in the average rate of temperature rise in the branch pipe occurs. Therefore, the temperature rise of the mixture flowing through the same distance is reduced. And $\Delta Ti$ is the product of the magnitude of the temperature rise of the mixture and the length of the branch pipe. That is for the longest branch, and the change of $\Delta Ti$ of the other branch pipes is the combination of the above changes, and the change factor of the branch length of the long branch is larger than the change factor the temperature rise of the mixed gas in the short branch. In general, the temperature $\Delta Ti$ at the nozzle at the end of the longest branch changes most, i.e. the highest temperature point of the propylene ammonia distributor nozzle, and if the temperature is lower than the nitriding temperature, it can be considered that any position of the propylene ammonia distributor in the reactor is lower than the nitriding temperature.

The present invention will be described below by way of example in connection with the production of acrylonitrile with reference to the accompanying drawings, but the present invention is not limited to these drawings or the production of acrylonitrile.

As shown in FIG. 1, the main internal components of a typical propylene ammoxidation fluidized bed reactor 1 include: cyclone (not shown), cooling coil 7, fluid distributor 100 (i.e., a distributor of a propylene ammonia mixed gas), air distribution plate 6, and process air inlet 8. A fluid distributor 100 is located between the air distribution plate 6 and the cooling coil 7. The propylene ammonia mixed gas from a feedstock gas mixing system (not shown) enters a fluid distributor 10 from a fluid inlet of the fluid distributor, passes through a housing (also called as a reactor wall) 4 of the reactor through the fluid distributor 10, enters a catalyst bed layer from a nozzle arranged on a conduit of the fluid distributor 100, is fully mixed with process air introduced from a process air inlet 8, and undergoes an ammoxidation reaction to generate products such as acrylonitrile and the like in the presence of a catalyst.

As shown in FIG. 2, a prior art fluid distributor 100 generally comprises: fluid distributor fluid inlet 105, main pipe y (y-pipe), branch pipe z (branch pipe), open pore 103, and nozzles (not shown). The branch pipe is a gas-directing conduit directly communicated with the fluid of the nozzle and mainly plays a role of transporting the mixed gas to the nozzle. The branch pipes are usually non-branched gas-directing conduits and are arranged in the same cross-section of the reactor, on which the open pores 3 and thus the nozzles are evenly distributed in a certain manner, thereby achieving an even distribution of the nozzle openings in the same cross-section of the reactor. The y-pipe is a gas-directing conduit directly in fluid communication with the branch pipe and mainly functions to transport the mixed gas to the branch pipe. The y-pipe is usually a straight pipe, and the branch pipes are uniformly communicated with the y-pipe and are positioned in the same cross-section of the reactor with the branch pipes, so that the uniform distribution of the nozzle openings in the same cross-section of the reactor is achieved. In some fluid distributors, the y-pipe, in addition to being in fluid communication with the branch pipes, are also in fluid communication with the nozzles directly through the open pores 103 as with the branch pipes for achieving the uniform distribution of the aforementioned nozzle openings over the same cross-section of the reactor.

As shown in FIGS. 3A and 3B, in some fluid distributors of the prior art, the branched pipes are in the same cross-section of the reactor as the y-pipe, but are not in the same plane as fluid distributor flow inlet 105, so that head pipe x (x-pipe) is provided to introduce the propylene ammonia mixed gas from the distributor flow inlet into the y-pipe. According to an embodiment of the present invention, typically only one x-pipe is required and there are no branch pipes at other locations than at the ends in fluid communication with the y-pipe. The x-pipe is a gas-directing conduit directly in fluid communication with the y-pipe and mainly functions to transport the mixed gas to the y-pipe.

In these prior art fluid distributors, the propylene ammonia mixed gas enters from the propylene ammonia fluid distributor flow inlet 105, is uniformly dispersed into the reactor bed along the x-pipe, y-pipe, branch pipes, and finally through the nozzles via open pores 103 provided in the y-pipe and branch pipes. The heat exchange between the propylene ammonia mixed gas and the catalyst bed layer occurs in the process of uniformly sending the propylene ammonia mixed gas to the catalyst bed layer along the conduit of the fluid distributor, so that the temperature rises continuously until the mixed gas reaches the highest temperature before entering the reactor through the nozzle. The inventors of the present invention have discovered through research that only reactors having a diameter of less than 10 meters can be satisfied when using existing fluid distributors 100 such as those shown in FIGS. 2 and 3. As the reactor diameter is further increased, the risk of the propylene ammonia mixed gas in the fluid distributor 100 reaching the nitriding temperature increases significantly. Moreover, even in reactors with a diameter of less than 10 meters, there is a risk that the propylene ammonia mixed gas reaches the nitriding temperature.

According to an embodiment of the present invention, as shown in FIG. 4, the fluid distributor 10 comprises a fluid inlet 15, a feeding main pipe 12, a branch pipe 11, an open pore 13 and a connection portion 16, and optionally comprises a nozzle (not shown). In the fluid distributor of the present invention, the distributor fluid inlet 15 is connected in a gas-tight manner to a pipe from a feedstock gas mixing system to transport the mixture into the fluid distributor. According to an embodiment of the present invention, the fluid distributor may comprise one or more distributor fluid inlets 15, each distributor fluid inlet 15 being connected to a separate feeding main pipe 12. As shown in FIGS. 4 to 8, according to an embodiment of the present invention, one or more feeding main pipes 12 are connected to and in fluid communication with one or more distributor fluid inlet 15, respectively, and extend from the distributor fluid inlet 15 to both sides around the reactor wall. The plurality of branch pipes 11 are connected to the feeding main pipe 12 at different positions, and are in fluid communication with the feeding main pipe 12 to transport the propylene ammonia mixed gas into the branch pipes 11. The shape of the feeding main pipe 12 of the fluid distributor of the present invention is not particularly limited, but preferably takes the shape of a circular ring (FIGS. 4 and 6), a semicircular ring (FIGS. 5 and 7), or an arc (FIG. 8). The pipe diameter of the feeding main pipe is not particularly limited, but it is preferable that the pipe diameter of the feeding main pipe 12 is larger than that of the branch pipes 11 in view of the workability when connecting with the branch pipes 11.

According to an embodiment of the present invention, the branch pipes 11 are straight pipes passing through the reactor wall 4, and the branch pipes 11 do not have any branch pipes in the reactor inner cavity, except for the open pores and nozzles provided thereon. Also, the plurality of branch pipes 11 are not connected to each other or crossed each other in the reactor inner cavity. One end of the plurality of branch pipes 11 is connected to the feeding main pipe 12, and the other end extends through the reactor wall 4 toward the inside of the reactor. The specific position of the connection point of the branch pipe 11 to the feeding main pipe 12 is not particularly limited, and the branch pipe 11 may be connected to the feeding main pipe 12 outside the reactor or may be connected to the feeding main pipe 12 at the reactor wall. In the case where the branch pipes 11 are connected to the feeding main pipe 12 outside the reactor, the connection of the branch pipes 11 to the reactor wall is not particularly limited, and welding means commonly used in the art may be used, and the gas-tight connection as shown in FIGS. 9 and 10 may also be used.

According to an embodiment of the present invention, all the branch pipes 11 are preferably in the same cross-section of the reactor. More preferably, the fluid distributor fluid inlets 15, the feeding main pipes 12 and the branch pipes 11 are all in the same cross-section of the reactor.

According to an embodiment of the present invention, when the reactor diameter is small, the branch pipe 11 may take the form of entering from one side of the reactor cross-section and extending to the vicinity of the reactor wall on the other side, over the entire cross-section of the reactor, as shown in FIG. 8. At this time, the upper limit of the length of the branch pipe 11 (the extension length of the branch pipe 11 inside the reactor) is smaller than the diameter of the reactor.

According to an embodiment of the present invention, especially when the diameter of the reactor is large, in order to avoid the temperature of the mixed gas reaching the nitriding temperature due to the long length of the branch pipe and the long path length of the mixed gas in the branch pipe, an arrangement as shown in FIG. 4 or FIG. 5 may be adopted. In FIGS. 4 and 5, in the cross-section of the reactor, the plurality of branch pipes 11 are divided into two groups, which pass through the reactor wall 4 from both sides of the cross-section and extend to the vicinity of the central axis of the cross-section perpendicular to the extension direction of the branch pipes 11, respectively. According to an embodiment of the present invention, it is preferable that the branch pipes 11 respectively arranged correspondingly at the above-mentioned both sides of the cross-section are symmetrical to each other. At this time, the length of the branch pipe 11 is preferably smaller than the radius of the reactor. As shown in FIGS. 4, 5 and 8, according to an embodiment of the present invention, a plurality of branch pipes 11 are not connected or crossed with each other inside the reactor, and, preferably, a plurality of branch pipes 11 are parallel to each other. More preferably, the vertical distances between the branch pipes 11 adjacent in the direction perpendicular to the extension direction of the branch pipes 11 are identical. The vertical distance is preferably 250-750 mm, preferably 300-650 mm, and more preferably 350-550 mm.

According to an embodiment of the present invention, it is also possible for the form of a fluid distributor to divide the cross-section of the reactor inner cavity into a plurality of sectors (for example 2 or more, in particular 2-8, 2-6 or 2-4), and to arrange a plurality of branch pipes 11 in parallel in each sector, as shown in FIG. 6 or FIG. 7. According to an embodiment of the present invention, the cross-section of the reactor is preferably divided into 4 sectors (four quadrants). The vertical distance between the adjacent branch pipes in the same quadrant is identical, and is preferably 250-750 mm, preferably 300-650 mm, and more preferably 350-550 mm.

As shown in FIGS. 4 to 8, according to an embodiment of the present invention, one or more open pores 13, called as orifices, are arranged in the branch pipe 11 along the axial direction thereof for injecting the mixture gas from the fluid distributor into the reactor.

According to an embodiment of the present invention, the perpendicular distance in the axial direction between the centers of the adjacent open pores in the axial direction of the branch pipe 11 on the branch pipe 11 is referred to as a pore distance. According to an embodiment of the present invention, the pore distance of adjacent open pores in the axial direction of any branch pipe is identical for any fluid distributor. The ratio of the pore distance between the adjacent open pores to the vertical distance between the adjacent parallel branch pipes is 1/N, and N is an integer of 2 or more. According to an embodiment of the present invention, N is preferably 2, i.e. the pore distance between adjacent open pores is half the vertical distance between the aforementioned adjacent parallel branch pipes. In other embodiments of the present invention, it is preferable that N is 3, i.e., the pore distance between the adjacent open pores is one third of the vertical distance between the adjacent parallel branch pipes.

According to an embodiment of the present invention, one or more open pore 13 may be arranged in the same radial cross-section of the branch pipe 11 (the cross-section corresponding to the center of the open pores is called the open pore cross-section). These open pores 13, which are in the same radial cross-section, are likewise connected to the respective nozzles and are concentric with them. According to an embodiment of the present invention, the same number of open pores are arranged on the same radial cross-section of the branch pipe 11 of the fluid distributor, and the open pores on the same radial cross-section are in one-to-one correspondence with the open pores on the other radial cross-sections, respectively, so as to be arranged in a row in the axial direction of the corresponding branch pipe, and the row is parallel to the axis of the branch pipe.

According to an embodiment of the present invention, in the fluid distributor shown in FIGS. 4 to 8, the pore-diameter of the open pores at different branch pipes or different radial cross-sections of the same branch may be identical or different.

According to an embodiment of the present invention, in the fluid distributor, the branch pipes 11 may be provided with nozzles as needed, and thus the lower pipe diameter limit of the branch pipes is preferably 70 mm or more, more preferably 75 mm or more, in view of the workability of the fluid distributor. When the diameter is less than this diameter, the branch pipe has poor workability, and it is difficult to install the nozzle. Meanwhile, in view of not affecting the fluidization effect, the upper limit of the pipe diameter of the branch pipe is preferably 145 mm or less, more preferably 135 mm or less.

According to an embodiment of the present invention, the diameter of all the branch pipes 11 inside the reactor is identical. On the other hand, in order to make the distribution of the propylene ammonia mixed gas in the whole reactor bed more uniform, According to an embodiment of the present invention, it is possible to arrange branch pipes 11 with one or more diameters in the same fluid distributor, as the case may be. Furthermore, According to an embodiment of the present invention, it is possible to have one or more different diameters of the same branch pipe 11 in the extension direction thereof.

According to an embodiment of the present invention, in order to control the distribution of the propylene ammonia mixed gas in the catalyst bed layer in the reactor, a fluid flow controller 14 may be provided at the fluid inlet 15 of the distributor for controlling the flow rate of the propylene ammonia mixed gas in the fluid distributor. In addition, in order to make the propylene ammonia mixed gas distributed more uniformly in the whole reactor bed, as shown in FIG. 9, a fluid flow controller 14 may be provided at a position of each branched pipe 11 outside the reactor according to an embodiment of the present invention.

EXAMPLES

The present invention will be described in further detail below by way of examples and comparative examples, but the present invention is not limited to the following examples.

All the following example data are obtained by simulating the conditions in different-diameter ammoxidation fluidized bed reactors in a laboratory, simulating an actual fluid distributor made of carbon steel according to the various fluid distributors shown in the drawings of the specification, and arranging temperature transmitters at important points to measure the temperature of the fluid distributor. In the following examples and comparative examples, all data were averaged after multiple measurements.

In the following embodiments, the branch pipe length refers to the length of the inner pipe segment of the branch pipe.

Example 1

The diameter of the propylene ammoxidation fluidized bed reactor (the diameter of the inner cavity, the same shall apply hereinafter) was 10 meters, a SANC series acrylonitrile catalyst of Sinopec Shanghai Research Institute of Petrochemical Technology was used for producing acrylonitrile, the reaction device run at full load, the mixing ratio of the feedstock gas of C3H6:NH3:air was 1:1.2:9.3, the reaction temperature was 440° C., the reaction pressure was 50 KPa, and the inlet temperature of the mixed gas fluid of propylene and ammonia was controlled to be 80° C. The fluid distributor adopted the form of FIG. 4, the material was carbon steel, the distributor was provided with 1 main pipe, the diameter of the main pipe was φ500 mm, 52 branch pipes were arranged and were respectively connected with the main pipe, the diameter of branch pipes was φ80 mm, the distance between the branch pipes was 380 mm, the branch pipes were parallel to each other, the open pore distance of the nozzles along the direction of the branch pipes was 190 mm, 52 nozzles were arranged on the longest branch pipe with the length of 4.9 m, 15 nozzles were arranged on the shortest branch pipe with the length of 1.8 m, the total number of the nozzles of the distributor was 2100, the inner diameter of the nozzles was 20 mm, the length was 200 mm; the hole-diameter of the orifice was 6.0 mm. The propylene ammonia mixed gas reached the terminal end nozzle (not shown in FIG. 4) of each branch pipe through the fluid distributor, and the temperature of the propylene ammonia mixed gas at the terminal end nozzle of each branch pipe was measured by a thermocouple, wherein the highest point temperature of the mixed gas in the fluid distributor was 282° C. which was the temperature of the propylene ammonia mixed gas at the terminal end nozzle of the branch pipe with the longest travel length.

Example 2

The diameter of the propylene ammoxidation fluidized bed reactor was 12 meters, a SANC series acrylonitrile catalyst of Sinopec Shanghai Research Institute of Petrochemical Technology was used for producing acrylonitrile, the reaction device run at full load, the mixing ratio of the feedstock gas of C3H6:NH3:air was 1:1.2:9.5, the reaction temperature was 440° C., the reaction pressure was 50 KPa, and the inlet temperature of the mixed gas fluid of propylene and ammonia was controlled to be 80° C. The fluid distributor adopted the form of FIG. 5, the material was carbon steel, the distributor was provided with 2 main pipes, the diameter of the main pipe was φ420 mm, 60 branch pipes were arranged and were respectively connected with the main pipe, the diameter of branch pipes was φ100 mm, the distance between the branch pipes was 410 mm, the branch pipes were parallel to each other, the open pore distance of the nozzles along the direction of the branch pipes was 205 mm, 58 nozzles were arranged on the longest branch pipe with the length of 5.9 m, 15 nozzles were arranged on the shortest branch pipe with the length of 1.9 m, the total number of the nozzles of the distributor was 2560, the inner diameter of the nozzles was 20 mm, and the length was 180 mm; the hole-diameter of the orifice was 6.2 mm. The propylene ammonia mixed gas reached the terminal end nozzle of each branch pipe through the fluid distributor, and the temperature of the propylene ammonia mixed gas at the terminal end nozzle of each branch pipe was measured by a thermocouple, wherein the highest point temperature of the mixed gas in the fluid distributor was 282° C. which was the temperature of the propylene ammonia mixed gas at the terminal end nozzle of the branch pipe with the longest travel length.

Example 3

The diameter of the propylene ammoxidation fluidized bed reactor was 15 meters, a SANC series acrylonitrile catalyst of Sinopec Shanghai Research Institute of Petrochemical Technology was used for producing acrylonitrile, the reaction device run at full load, the mixing ratio of the feedstock gas of C3H6:NH3:air was 1:1.2:9.5, the reaction temperature was 435° C., the reaction pressure was 55 KPa, and the inlet temperature of the mixed gas fluid of propylene and ammonia was controlled to be 80° C. The fluid distributor adopted the form of FIG. 6, the material was carbon steel, the distributor was provided with 1 main pipe, the diameter of the main pipe was φ650 mm, 44 branch pipes were arranged and were respectively connected with the main pipe, the diameter of branch pipes was φ100 mm, the distance between the branch pipes was 690 mm, the branch pipes were parallel or vertical to each other, the open pore distance of the nozzles along the direction of the branch pipes was 230 mm, 96 nozzles were arranged on the longest branch pipe with the length of 7.45 m, 45 nozzles were arranged on the shortest branch pipe with the length of 2.4 m, the total number of the nozzles of the distributor was 3008, the inner diameter of the nozzles was 20 mm, and the length was 150 mm; the hole-diameter of the orifice was 6.5 mm. The propylene ammonia mixed gas reached the terminal end nozzle of each branch pipe through the fluid distributor, and the temperature of the propylene ammonia mixed gas at the terminal end nozzle of each branch pipe was measured by a thermocouple, wherein the highest point temperature of the mixed gas in the fluid distributor was 298° C. of the temperature of the propylene ammonia mixed gas at the terminal end nozzle of the branch pipe with the longest travel length.

Example 4

The diameter of the propylene ammoxidation fluidized bed reactor was 20 meters, a SANC series acrylonitrile catalyst of Sinopec Shanghai Research Institute of Petrochemical Technology was used for producing acrylonitrile, the reaction device run at full load, the mixing ratio of the feedstock gas of C3H6:NH3:air was 1:1.2:9.5, the reaction temperature was 435° C., the reaction pressure was 55 KPa, and the inlet temperature of the mixed gas fluid of propylene and ammonia was controlled to be 80° C. The fluid distributor adopted the form of FIG. 7, the material was carbon steel, the distributor was provided with 2 main pipes, the diameter of the main pipe was φ500 mm, 84 branch pipes were arranged and were respectively connected with the main pipe, the diameter of branch pipes was φ120 mm, the distance between the branch pipes was 460 mm, the branch pipes were parallel or vertical to each other, the open pore distance of the nozzles along the direction of the branch pipes was 230 mm, 84 nozzles were arranged on the longest branch pipe with the length of 9.8 m, 20 nozzles were arranged on the shortest branch pipe with the length of 2.9 m, nozzles 5740, the inner diameter of the nozzles was 20 mm, and the length was 150 mm; the hole-diameter of the orifice was 6.6 mm. And The propylene ammonia mixed gas reached the terminal end nozzle of each branch pipe through the fluid distributor, and according to HTFS calculation of a model and the existing experimental data, the highest point temperature of the mixed gas in the fluid distributor was 316° C. of the temperature of the propylene ammonia mixed gas at the terminal end nozzle of the branch pipe with the longest travel length.

Example 5

The diameter of the propylene ammoxidation fluidized bed reactor was 20 meters, a SANC series acrylonitrile catalyst of Sinopec Shanghai Research Institute of Petrochemical Technology was used for producing acrylonitrile, the reaction device run at full load, the mixing ratio of the feedstock gas of C3H6:NH3:air was 1:1.2:9.5, the reaction temperature was 435° C., the reaction pressure was 55 KPa, and the inlet temperature of the mixed gas fluid of propylene and ammonia was controlled to be 100° C. The fluid distributor adopted the form of FIG. 7, 3 open pores were arranged on the same cross-section of the branch pipes, the distance between the adjacent parallel branch pipes was 750 mm, the pore distance between the adjacent open pores was 250 mm, the material was carbon steel, the distributor was provided with 2 main pipes, the diameter of the main pipe was φ500 mm, the diameter of branch pipes was φ130 mm, the number of the branch pipes was 52, the branch pipes were parallel or vertical to each other, 120 nozzles were arranged on the longest branch pipe with the length of 9.8 m, 43 nozzles were arranged on the shortest branch pipe with the length of 4.3 m, nozzles 4880, the inner diameter of the nozzles was 20 mm, and the length was 150 mm; the hole-diameter of the orifice was 6.5 mm. And The propylene ammonia mixed gas reached the terminal end nozzle of each branch pipe through the fluid distributor, and according to HTFS calculation of a model and the existing experimental data, the highest point temperature of the mixed gas in the fluid distributor was 305° C. of the temperature of the propylene ammonia mixed gas at the terminal end nozzle of the branch pipe with the longest travel length.

Comparative Example 1

The diameter of the propylene ammoxidation fluidized bed reactor was 15 meters, a SANC series acrylonitrile catalyst of Sinopec Shanghai Research Institute of Petrochemical Technology was used for producing acrylonitrile, the reaction device run at full load, the mixing ratio of the feedstock gas of C3H6:NH3:air was 1:1.2:9.5, the reaction temperature was 435° C., the reaction pressure was 55 KPa, and the inlet temperature of the mixed gas fluid of propylene and ammonia was controlled to be 80° C. The fluid distributor adopted the form of FIGS. 3A and 3B, the material was carbon steel, the diameter of the x pipe was φ500 mm, the diameter of the y pipe was φ250 mm, the diameter of branch pipes was φ100 mm, the number of the branch pipes was 66, the distance between the branch pipes was 460 mm, and the open pore distance of the nozzles was 230 mm; 64 nozzles were arranged on the longest branch pipe with the length of 7.45 m, 18 nozzles were arranged on the shortest branch pipe with the length of 2.0 m, the total number of the nozzles of the distributor was 3008, the inner diameter of the nozzles was 20 mm, and the length of each nozzle was 200 mm; the hole-diameter of the orifice was 6.5 mm. The propylene ammonia mixed gas reached the terminal end nozzle of each branch pipe through a fluid distributor pipeline, and the highest temperature of the mixed gas in the fluid distributor was 355° C. according to HTFS calculation of a model and the existing experimental data.

Comparative Example 2

The diameter of the propylene ammoxidation fluidized bed reactor was 15 meters, a SANC series acrylonitrile catalyst of Sinopec Shanghai Research Institute of Petrochemical Technology was used for producing acrylonitrile, the reaction device run at full load, the mixing ratio of the feedstock gas of C3H6:NH3:air was 1:1.2:9.5, the reaction temperature was 435° C., the reaction pressure was 55 KPa, and the inlet temperature of the mixed gas fluid of propylene and ammonia was controlled to be 80° C. The fluid distributor adopted the form of FIG. 2, the material was carbon steel, the diameter of the y pipe was φ250 mm, the diameter of branch pipes was φ100 mm, the number of the branch pipes was 66, the distance between the branch pipes was 460 mm, the open pore distance of the nozzles was 230 mm, 64 nozzles were arranged on the longest branch pipe with the length of 7.45 m, 18 nozzles were arranged on the shortest branch pipe with the length of 2.0 m, the total number of the nozzles of the distributor was 3008, the inner diameter of the nozzles was 20 mm, and the length was 200 mm; the hole-diameter of the orifice was 6.5 mm. The propylene ammonia mixed gas reached the terminal end nozzle of each branch pipe through a fluid distributor pipeline, and the highest temperature of the mixed gas in the fluid distributor was 348° C. according to HTFS calculation of a model and the existing experimental data.

In examples 1 to 4 to which the propylene ammonia fluid distributor of the present invention was applied, the temperature $T_i$ of the propylene ammonia mixed gas at any point of the fluid distributor was lower than 350° C., i.e., lower than the temperature at which ammonia decomposes into active nitrogen atoms, even when the reactor diameter was much larger than that of the conventional propylene ammoxidation reactor. In contrast, in comparative examples 1 and 2, the temperature of the propylene ammonia within the fluid distributor reached the nitriding temperature, which presented a risk of nitriding embrittlement of the fluid distributor, when the prior art fluid distributor version was used.

The invention claimed is:
1. A fluid distributor adapted to transport a fluid to a vessel inner cavity, comprising:
   one or more fluid transport main pipe(s); either one fluid transport main pipe is configured to form a closed shape, when its centerline and/or centerline extension thereof are joined end-to-end; or a plurality of fluid transport main pipes are configured to form a closed shape, when their respective centerlines and/or centerline extensions thereof are joined end-to-end, and each of the fluid transport main pipe(s) has at least one fluid inlet, a plurality of fluid transport branch pipes disposed on each of said fluid transport main pipes, each of said fluid transport branch pipes having a starting end and a terminal end, said starting end being connected to and in fluid communication with said fluid transport main pipe and said starting end and said terminal end defining a length L of said fluid transport branch pipe,
   a plurality of open pores disposed along the length of said fluid transport branch pipe in each of said fluid transport branch pipes, and
   a connection portion provided on each of the fluid transport branch pipes, the connection portion being configured to connect the fluid transport branch pipe to housing after the fluid transport branch pipe passes through the housing of the vessel into the inner cavity.
2. The fluid distributor of claim 1, wherein the inner diameters of the plurality of fluid transport main pipes are identical to or different from each other, and are each independently 150-700 mm.
3. The fluid distributor of claim 1, wherein on each of the fluid transport branch pipes, the plurality of open pores are arranged along the length direction of the fluid transport branch pipe on a pipe segment of the fluid transport branch pipe from the connection portion to the terminal end.

4. The fluid distributor of claim 1, wherein the inner segment of at least one of the fluid transport branch pipes has a constant or varying inner diameter in a direction from the connection portion to the terminal end of the fluid transport branch pipe, and/or the length Li of the inner segment is such that after the fluid transport branch pipe passes through the housing of the vessel and enters the inner cavity, two intersection points are generated between the extension line of the central line of the inner pipe segment towards the head and tail ends of the pipe segment and the inner surface of the housing, and the length of the line segment between the two intersection points is Ld, so that 0<Li<Ld.

5. The fluid distributor of claim 1, wherein on each of said fluid transport main pipes, said plurality of fluid transport branch pipes are divided into one or more groups, such that in any one group of fluid transport branch pipes, i) the centerlines of any two adjacent fluid transport branch pipes are parallel or substantially parallel to each other along the same direction (referred to as the extension direction of the group of fluid transport branch pipes), and/or, ii) the inner diameters of any two adjacent fluid transport branch pipes are identical to or different from each other, each independently being 50-150 mm, and/or, iii) the perpendicular distances D2 of the centerlines of any two adjacent fluid transport branch pipes are identical to or different from each other, each independently being 250-750 mm, and/or iv) the D1 and the D2 satisfy the relation: D1/D2≥0.3, and/or, v) the ends of two adjacent fluid transport branch pipes are connected end-to-end to form a line segment having the shape of a fold line or a straight line, and/or vi) the length of the longest fluid transport branch pipe in the group of fluid transport branch pipes is 5000-29000 mm.

6. The fluid distributor of claim 1, wherein on each of said fluid transport main pipes, said plurality of fluid transport branch pipes is divided into one or more groups, or all fluid transport branch pipes of said fluid distributor are divided into one or more groups, then between said groups of fluid transport branch pipes i) the extension directions of one group of fluid transport branch pipes and the other group of fluid transport branch pipes form an angle with each other, and/or ii) the projection of one group of fluid transport branch pipes onto said closed shape does not overlap the projection of the other group of fluid transport branch pipes onto said closed shape.

7. The fluid distributor of claim 1, wherein the centerline of each of the fluid transport branch pipes is substantially a straight line.

8. The fluid distributor of claim 1, wherein the plurality of open pores are identical to or different from each other on each of the fluid transport branch pipes, each independently having a peripheral shape selected from the group consisting of circular, oval, square, rectangular, trapezoidal, and diamond, and/or the plurality of open pores are identical to or different from each other, each independently having an equivalent circular diameter of 3-10 mm.

9. The fluid distributor of claim 1, wherein on at least one of said fluid transport branch pipes, a fluid flow controller is provided on the pipe segment of said fluid transport branch pipe from the connection portion to the starting end (referred to as the outer pipe segment).

10. The fluid distributor of claim 1, wherein the connection portion is configured to have a shape surrounding the fluid transport branch, or the closed shape has a diameter of 5.5-32.0 meters.

11. The fluid distributor of claim 1, further comprising a nozzle disposed surrounding the open pore.

12. The fluid distributor of claim 1, wherein the vessel is a fluidized bed reactor, the diameter of the inner cavity of the reactor is 5-29 meters and the fluid is a nitrogen-containing gas or an ammonia-containing gas.

13. A method of using the fluid distributor of claim 1 to transport a fluid to a vessel inner cavity, comprising the step of transporting a fluid to the at least one fluid inlet of the fluid distributor, the fluid passing into the inner cavity through at least the fluid transport main pipe, the fluid transport branch pipes and the open pores.

14. A method for feeding a reaction feed into an ammoxidation reactor, comprising feeding the reaction feed through the fluid distributor according to claim 1 into an inner cavity of the ammoxidation reactor.

15. A reaction apparatus comprising a reactor and the fluid distributor of claim 1, wherein the reactor has at least a housing, a plurality of through-holes provided in the housing, and an inner cavity defined by an inner surface of the housing, the through-holes having a one-to-one correspondence relationship in number and arrangement positions with fluid transport branch pipes of the fluid distributor, whereby each fluid transport branch pipe enters the inner cavity through one through-hole corresponding thereto, and the fluid transport branch pipe is air-tightly fixed on the outer surface of the housing by a connection portion of the fluid transport branch pipe after passing through the through-hole.

16. A process for producing acrylonitrile, comprising the steps of feeding a propylene ammonia mixed gas into the inner cavity of a reactor and feeding an oxygen-containing gas into the inner cavity of the reactor by using the fluid distributor according to claim 1.

17. A process for producing acrylonitrile, comprising the steps of feeding a propylene ammonia mixed gas into the inner cavity of a reactor and feeding an oxygen-containing gas into the inner cavity of the reactor by using the fluid distributor according to the process according to claim 13.

18. A process for producing acrylonitrile in the reaction apparatus according to claim 15, comprising the steps of feeding a propylene ammonia mixed gas into the inner cavity of the reactor and feeding an oxygen-containing gas into the inner cavity of the reactor by using the fluid distributor.

19. The fluid distributor of claim 1, wherein the number of said fluid transport main pipe(s) is 1-8, and/or, either one fluid transport main pipe is configured to form a substantially planar closed shape when its centerline and/or centerline extension thereof are joined end-to-end, or a plurality of fluid transport main pipes are configured to form a substantially planar closed shape when their respective centerlines and/or centerline extensions thereof are joined end-to-end, and/or, each of said fluid transport main pipe(s) has 1-3 fluid inlet(s), and/or, the number of said plurality of fluid transport branch pipes disposed on each of said fluid transport main pipes is 5-100, and/or, the terminal end is in a closed, semi-closed or open configuration, and/or, the number of the plurality of open pores disposed along the length of said fluid transport branch pipe in each of said fluid transport branch pipes is 2-140, and/or, the connection portion is provided at a postion closer to the starting end than the terminal end, and/or, the connection portion is configured to fix the fluid transport branch pipe to the outer surface of the housing after the fluid transport branch pipe passes through the housing of the vessel into the inner cavity.

20. The fluid distributor of claim 1, wherein the number of said fluid transport main pipe(s) is 1-2, and/or, either one fluid transport main pipe is configured to form a substantially planar circular, elliptical or polygonal shape that is substantially perpendicular to the vessel centerline when its centerline and/or centerline extension thereof are joined end-to-end or a plurality of fluid transport main pipes are configured to form a substantially planar circular, elliptical or polygonal shape that are substantially perpendicular to the vessel centerline when their respective centerlines and/or centerline extensions thereof are joined end-to-end, and/or, each of said fluid transport main pipe(s) has 1 fluid inlet, and/or, the number of the plurality of fluid transport branch pipes disposed on each of said fluid transport main pipes is 5-50, and/or the terminal end is in a closed configuration, and/or, the number of the plurality of open pores disposed along the length of said fluid transport branch pipe in each of said fluid transport branch pipes is 6-60, and/or, the connection portion is provided at a distance from the starting end along the length direction of the fluid transport brance pipe of ¼ or less, or ¹⁄₁₀ or less of the length L of the fluid transport branch pipe, and/or, the connection portion is configured to affix the fluid transport branch pipe to the outer surface of the housing after the fluid transport branch pipe passes through the housing of the vessel into the inner cavity.

21. The fluid distributor of claim 1, wherein the inner diameters of the plurality of fluid transport main pipes are identical to or different from each other, and are each independently 170-500 mm.

22. The fluid distributor of claim 3, wherein the distances D1 between any two adjacent open pores are identical to or different from each other, and are respectively and independently 175-250 mm.

23. The fluid distributor of claim 4, wherein the inner segment of at least one of the fluid transport branch pipes has a gradually increased or gradually decreased inner diameter in a direction from the connection portion to the terminal end of the fluid transport branch pipe, and/or, $0.25Ld \leq Li \leq 0.99Ld$.

24. The fluid distributor of claim 4, wherein $0.40 Ld \leq Li < 0.50 Ld$.

25. The fluid distributor of claim 5, wherein on each of said fluid transport main pipes, said plurality of fluid transport branch pipes are divided into 2-8 groups, and/or, the inner diameters of any two adjacent fluid transport branch pipes are identical to or different from each other, each independently being 65-125 mm, and/or, the perpendicular distances D2 of the centerlines of any two adjacent fluid transport branch pipes are identical to or different from each other, each independently being 300-650 mm, and/or, the D1 and the D2 satisfy the relation: $D1/D2 \geq 0.5$, and/or, the height difference between the highest point and the lowest point of the fold line is Hc, and the length of the longest fluid transport branch pipe in the group of fluid transport branch pipes is Lmax, then $Hc/Lmax \leq 44\%$, and/or, the length of the longest fluid transport branch pipe in the group of fluid transport branch pipes is 5000-20000 mm.

26. The fluid distributor of claim 25, wherein on each of said fluid transport main pipes, said plurality of fluid transport branch pipes are divided into 2-4 groups, and/or, the perpendicular distances D2 of the centerlines of any two adjacent fluid transport branch pipes are identical to or different from each other, each independently being 350-550 mm, and/or, Hc is substantially 0, and/or the length of the longest fluid transport branch pipe in the group of fluid transport branch pipes is 5000-10000 mm.

27. The fluid distributor of claim 1, wherein the ends of two adjacent fluid transport branch pipes are connected end-to-end to form a line segment having the shape of a straight line which is substantially perpendicular to the extension direction of the group of fluid transport branch pipes, and/or, the length of the longest fluid transport branch pipe in the group of fluid transport branch pipes is 6000-10000 mm.

28. The fluid distributor of claim 6, wherein on each of said fluid transport main pipes, said plurality of fluid transport branch pipes is divided into 2-8 groups, or all fluid transport branch pipes of said fluid distributor are divided into 2-8 groups, and/or, i) the extension directions of one group of fluid transport branch pipes and the other group of fluid transport branch pipes are parallel to each other or perpendicular to each other, and/or, ii) the sum At of the projected areas of all the groups of fluid transport branch pipes contained in the fluid distributor on the closed shape is smaller than the area Ac of the closed shape.

29. The fluid distributor of claim 28, wherein on each of said fluid transport main pipes, said plurality of fluid transport branch pipes is divided into 2-4 groups, or all fluid transport branch pipes of said fluid distributor are divided into 2-4 groups, and/or ii) At/Ac is 90% or more.

30. The fluid distributor of claim 8, wherein the plurality of open pores are identical to or different from each other, each independently have an equivalent circular diameter of 5.0-7.5 mm.

31. The fluid distributor of claim 9, wherein the fluid flow controller is a fluid flow control valve.

32. The fluid distributor of claim 10, wherein the connection portion is configured to have a flange shape, or the closed shape has a diameter of 13.0-23.0 meters.

33. The fluid distributor of claim 12, wherein the diameter of the inner cavity of the reactor is 5-20 meters, and/or, the fluid is a mixed gas of alkene and ammonia.

34. The fluid distributor of claim 12, wherein the diameter of the inner cavity of the reactor is 12-20 meters, and/or, the fluid is a propylene ammonia mixed gas.

35. The method of claim 13, wherein the fluid is a propylene ammonia mixed gas.

36. The process according to claim 16, wherein the reactor is a fluidized bed reactor, and/or, the oxygen-containing gas is air.

* * * * *